US006908992B2

(12) United States Patent
Koffas et al.

(10) Patent No.: US 6,908,992 B2
(45) Date of Patent: *Jun. 21, 2005

(54) METHANOTROPHIC CARBON METABOLISM PATHWAY GENES AND ENZYMES

(75) Inventors: Mattheos Koffas, Wilmington, DE (US); Kelley C. Norton, Avondale, PA (US); James M. Odom, Kennett Square, PA (US); Rick W. Ye, Wilmington, DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 158 days.

This patent is subject to a terminal disclaimer.

(21) Appl. No.: 10/320,924

(22) Filed: Dec. 17, 2002

(65) Prior Publication Data

US 2003/0129721 A1 Jul. 10, 2003

Related U.S. Application Data

(62) Division of application No. 09/934,901, filed on Aug. 22, 2001, now Pat. No. 6,555,353.
(60) Provisional application No. 60/229,906, filed on Sep. 1, 2000.

(51) Int. Cl.$^7$ .......................... C07H 21/04; C12N 9/88; C12N 1/21; C12N 1/15; C12N 15/52

(52) U.S. Cl. .................... 536/23.2; 435/232; 435/252.3; 435/252.31; 435/252.33; 435/252.34; 435/252.35; 435/254.11; 435/254.2; 435/254.21; 435/254.22; 435/254.23; 435/254.3; 435/320.1

(58) Field of Search .................. 536/23.2; 435/232, 435/252.3, 252.31, 252.33, 252.34, 252.35, 254.11, 254.2, 254, 21, 254.22, 254.23, 254.3, 320.1

(56) References Cited

U.S. PATENT DOCUMENTS 6,689,601 B2 * 2/2004 Koffas et al. ................ 435/247

FOREIGN PATENT DOCUMENTS

WO       WO 9633821 A1      10/1996

OTHER PUBLICATIONS

Green, Peter, Taxonomy of Methylotropyhic Bacteria, In: Methane and Methanol Utilizers (Biotechnology Handbooks 5), J. Colin Murrell and Howard Dalton eds. 1992, Pleanum Press NY. pp. 23–84.
Murrell et al., Molecular biology and regulation of methane monooxygenase, Arch. Microbiol. (2000), 173(5–6), 325–332.

Villadsen, John, Recent Trends Chem. React. Eng., (Proc. Int. Chem. React. Eng. Conf.), $2^{nd}$ (1987), vol. 2, 320–333, Editor(s): Kulkarni, B. D., Mashelkar, R. A.; Sharma, M. M., Publisher: Wiley East, New Delhi, India; Naguib, M., Proc. OAPEC Symp. Petroprotein, (Pap.) 1980, Meeting Date 1979, 253–77 Publisher: Organ. Arab Pet. Exporting Countries, Kuwait.
Tsien et al., Microbial Degradation of Low Moleuclar weight halogenated hydrocarbons, Gas, Oil, Coal, Environ. Biotechnol. 2, (Pap. Int. IGT Symp. Gas, Oil, Coal, Environ, Biotechnol.) $2^{nd}$ (1990), 83–104, Editor(s): Akin et al., Publisher: Inst. Gas Technol., Chicago, IL.
Merlkey et al., Biodegradation of Toxaphene under Methane Cometabolism and Denitrifying Conditions, Biorem. Recaicitrant Org.(Pap. Int. In Situ On–Site Bioreclam. Symp.), $3^{rd}$ (1995), 165–74, Editor(s) Hinchee et al., Publisher: Battelle Press, Columbus, OH.
Meyer et al., Development of techniques for the bioremediation of soil, air and groundwater polluted with chlorinated hydrocarbons: the demonstration project at the model site in Eppelheim, Microb. Releases, 1993, 2(1), 11–22.
Inanova et al., Production of Organic Exometabolites by diverse cultures of obligate methanotrophs, Mikrobiologiya (1998), 57(4), 600–5.
Kilbane, John, II , A biosystem for removal of metal ions from water, Gas, Oil, Coal, Environ. Biotechnol. 3, (Pap. IGT's Int. Symp.), $3^{rd}$ (1991), Meeting Date 1990, 207–26. Editor(s): Akin et al., Publisher: IGT, Chicago, IL.
Urakami et al., Occurrence of isoprenoid compounds in gramnegative methanol–, methane–, and methylamine–utilizing bacteria, J. Gen. Appl. Microbiol. 1986, 32(4), 317–41.
Dijkhuizen et al., (1992), The Physiology and biochemistry of aerobic methanol–utilizing gram negative and gram positive bacteria. In: Methane and Methanol utilizers. P. 149–Colin Murrell and Howard Dalton, Plenum Press NY.
Kohler, U., et al., Transaldolase genes from the cyanobacteria *Anabaena variabilis* and Synechocystis sp. PCC 6803; comparison with other eubacterial and eukaryotic homologues, Plant. Mol. Biol. 30(1) pp. 213–218, 1996.
Blattner, F. R. et al., The Complete Genome Sequence of *Escherichia coli* K–12, Sciencee 277: pp. 1453–1474, 1997.
Alefounder, P. R. et al., Identification, molecular cloning and sequence analysis of a gene cluster encoding the Class II fructose 1,6–bisphosphate aldolase, 3–phosphoglycerate kinase and a putative second glyceraldehyde 3–phosphate dehydrogenase of *Escherichia coli*, Mol. Microbiol. 3: pp. 723–732, 1989.

(Continued)

*Primary Examiner*—Elizabeth Slobodyansky

(57) ABSTRACT

Genes have been isolated from a *Methylomonas* sp encoding enzymes in the carbon flux pathway. The genes encode a 2-keto-3-deoxy-6-phosphogluconate (KDPGA) and a fructose bisphosphate aldolase (FFBPA), as well as numerous other genes. The genes will be useful in C1 metabolizing microorganisms for the manipulation of the carbon flux pathway.

7 Claims, 1 Drawing Sheet

OTHER PUBLICATIONS

Figure 1:
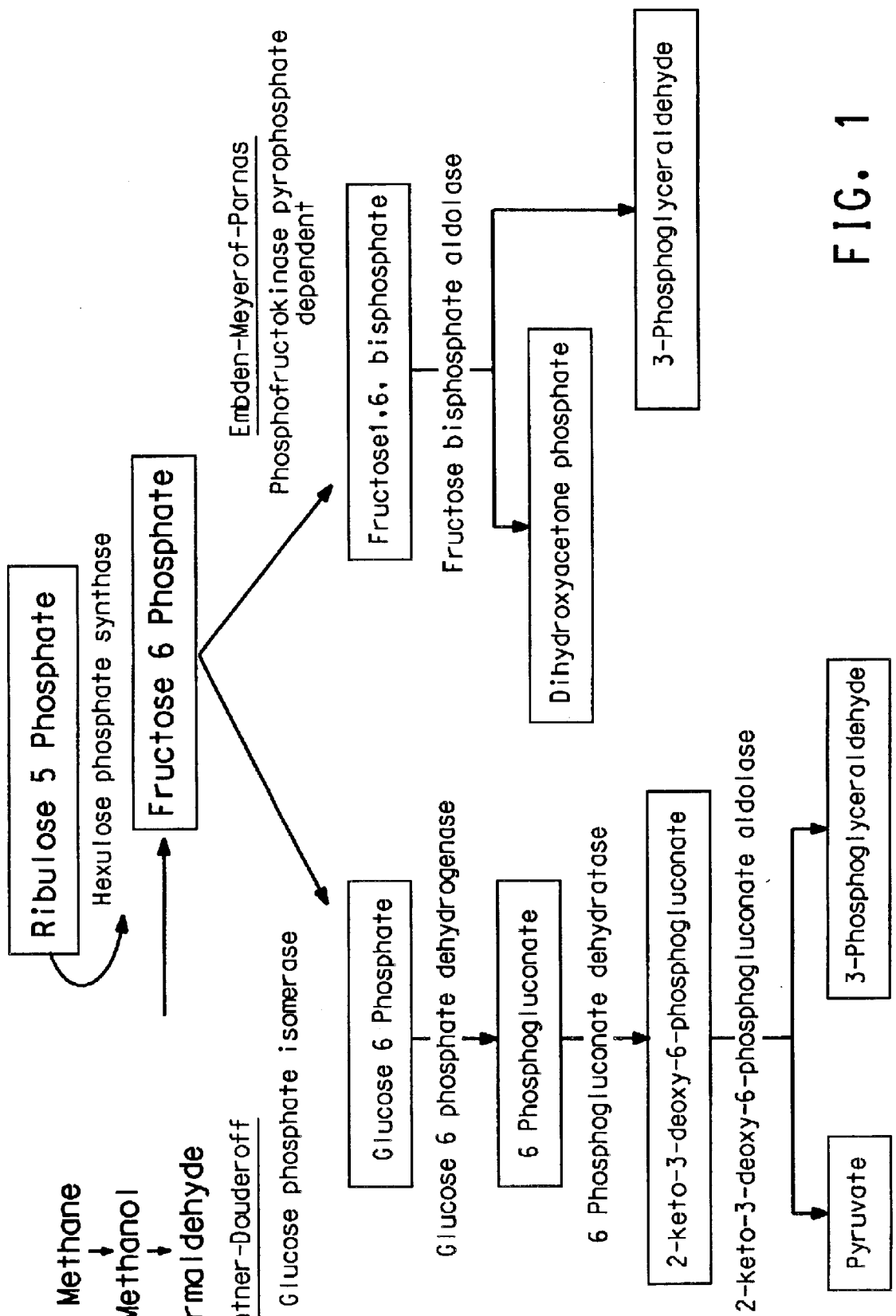

Van den berg, E. R. et al., Primary Structure and Phylogeny of the Calvin Cycle Enzymes Transketolase and Fructose-blsphosphate Aldolase of *Xanthobacter flavus*, J. Bacteriol. 178: pp. 888–893, 1996.

Redenbach et al., A set of ordered cosmid and adetailed genetic and physical map for the 8 MbStreptomyces coelicolor A3(2) chromosome, Mol. Microbiol. 21(1), pp. 77–96, 1996.

Lepek et al., Direct Submission, Acc. No. AF268969.1, *Mesorhizobium loti*, Jun. 2, 2001.

Blattner et al., Analysis of the *Escherichia coli* genome. IV DNA sequence of the region from 89.2 to 92.8 minutes, Nucleic Acids Res. 21(23), pp. 5408–5417, 1993.

Ladror et al., Cloning, Sequencing, and Expression of Pyrophosphate–dependent Phosphofructokinase from *Propionibacterium freudenreichii*, J. Biol. Chem. 226, pp. 16550–16555, 1991.

Willis et al., A Novel *Sinorhizobium melitoti* Operon Encodes an α–Glucosidase and a Periplasmic–Binding–Protein–Dependent Transport System for α–glucosides, J. Bacteriol. 181(14), 4176–4184, 1999.

Hugouvieux–Cotte–Pattat, N, Title Direct Submission, gll397854lemblCAA52858.1 (X74866), Jan. 31, 1994.

Koehler et al., Transaldolase Genes from the Cyanobacteria *Anabaena variabills* and Synechocystis sp PCC 6903: Comparison with other Eubacterial and Eukaryotic Homologues, Plant Molecular Biology, vol. 30, pp. 213–218, 1996 XP000960916.

Shishkina et al., Effect of Glucose on the Growth and Metabolism of Obligate Methanotrophs, XP002197432, Mikrobiologlya, vol. 57, No. 6, 1988, pp. 917–923.

Hanson et al., Methanotrophic bacteria, Microbiological Reviews, vol. 60, No. 2, 1996, pp. 439–471, XP002197430.

Trotsenko et al., "Biology of extremeophilic and extremotolerant methanotrophs", Archives of Microbiology, vol. 177, No. 2, pp. 123–131, Feb. 2002, XP002197431.

* cited by examiner

METHANOTROPHIC CARBON METABOLISM PATHWAY GENES AND ENZYMES

This application is a divisional of application Ser. No. 09/934,901 filed Aug. 22, 2001 now U.S. Pat. No. 6,555,353 which claims the benefit of U.S. Provisional Application No. 60/229,906, filed Sep. 1, 2000.

FIELD OF THE INVENTION

The invention relates to the field of molecular biology and microbiology. More specifically, the invention relates to genes involved in the conversion of hexose sugars into 3-carbon metabolites in methanotrophic bacteria.

BACKGROUND OF THE INVENTION

Methanotrophic bacteria are defined by their ability to use methane as their sole source of carbon and energy. Although methanol is an obligate intermediate in the oxidation of methane, the ability to grow on methanol alone is highly variable among the obligate methanotrophs (Green, Peter. Taxonomy of Methylotrophic Bacteria. In: Methane and Methanol Utilizers (Biotechnology Handbooks 5) J. Colin Murrell and Howard Dalton eds. 1992 Pleanum Press NY. pp. 23–84)). The conversion of C1 compounds to complex molecules with C—C bonds is difficult and expensive by traditional chemical synthetic routes. Traditionally, methane is first converted to synthesis gas which is then used to produce other small molecular weight industrial precursors. The basic problem is activation of the methane molecule, a process which is thermodynamically very difficult to achieve by chemical means. Methanotrophs have proved useful mediators of this problem.

Methane monooxygenase is the enzyme required for the primary step in methane activation and the product of this reaction is methanol (Murrell et al., *Arch. Microbiol.* (2000), 173(5–6), 325–332). This remarkable reaction occurs at ambient temperatures and pressures, whereas chemical transformation of methane to methanol requires temperatures of hundreds of degrees and high pressures (Grigoryan, E. A., *Kinet. Catal.* (1999), 40(3), 350–363; WO 2000007718; U.S. Pat. No. 5,750,821). It is this ability to transform methane under ambient conditions, along with the abundance of methane, that makes the biotransformation of methane a potentially unique and valuable process.

The commercial applications of biotransformation of methane have historically fallen broadly into three categories: 1) Production of single cell protein, (Villadsen, John, *Recent Trends Chem. React. Eng.*, [Proc. Int. Chem. React. Eng. Conf.], 2nd (1987), Volume 2, 320–33. Editor(s): Kulkarni, B. D.; Mashelkar, R. A.; Sharma, M. M. Publisher: Wiley East, New Delhi, India; Naguib, M., Proc. OAPEC Symp. Petroprotein, [Pap.] (1980), Meeting Date 1979, 253–77 Publisher: Organ. Arab Pet. Exporting Countries, Kuwait, Kuwait); 2) epoxidation of alkenes for production of chemicals (U.S. Pat. No. 4,348,476); and 3) biodegradation of chlorinated pollutants (Tsien et al., *Gas, Oil, Coal, Environ. Biotechnol.* 2, [Pap. Int. IGT Symp. *Gas, Oil, Coal, Environ. Biotechnol.*], 2nd (1990), 83–104, Editor(s): Akin, Cavit; Smith, Jared. Publisher: Inst. Gas Technol., Chicago, Ill.; WO 9633821; Merkley et al., *Biorem. Recalcitrant Org.*, [Pap. Int. In Situ On-Site Bioreclam. Symp.], 3rd (1995), 165–74. Editor(s): Hinchee, Robert E; Anderson, Daniel B.; Hoeppel, Ronald E. Publisher: Battelle Press, Columbus, Ohio; Meyer et al., *Microb. Releases* (1993), 2(1), 11–22). Only epoxidation of alkenes has experienced little commercial success due to low product yields, toxicity of products and the large amount of cell mass required to generate product.

Methanotrophic cells can further build the oxidation products of methane (i.e. formaldehyde) into more complex molecules such as protein, carbohydrate and lipids. For example, under certain conditions methanotrophs are known to produce exopolysaccharides (Ivanova et al., *Mikrobiologiya* (1988), 57(4), 600–5); Kilbane, John J., II Gas, *Oil, Coal, Environ. Biotechnol.* 3, [Pap. IGT's Int. Symp.], 3rd (1991), Meeting Date 1990, 207–26. Editor(s): Akin, Cavit; Smith, Jared. Publisher: IGT, Chicago, Ill.). Similarly, methanotrophs are known to accumulate both isoprenoid compounds and carotenoid pigments of various carbon lengths (Urakami et al., *J. Gen. Appl. Microbiol.* (1986), 32(4), 317–41). Although these compounds have been identified in methanotrophs, they have not been microbial platforms of choice for production because these organisms have very poorly developed genetic systems, thereby limiting metabolic engineering ability for chemicals.

A necessary prerequisite to metabolic engineering of methanotrophs is a full understanding, and optimization, of the carbon metabolism for maximum growth and/or product yield. In methanotrophic bacteria, methane is converted to biomolecules via a cyclic set of reactions known as the ribulose monophosphate pathway (RuMP) cycle. The RuMP pathway is comprised of three phases, each phase being a series of enzymatic steps. The first phase (fixation) is the aldol condensation of three molecules of C-1 (formaldehyde) with three molecules of pentose (ribulose-5-phospate) to form three molecules of a six-carbon sugar (fructose-6-phosphate) catalyzed by hexulose monophosphate synthase. This fixation phase is common to all methylotrophic bacteria using the RuMP pathway.

The second phase is termed "cleavage" and results in splitting of that 6-carbon sugar into two 3-carbon molecules. This may be achieved via two possible routes. Fructose-6-phosphate is either converted into fructose-1,6-biphosphate (FBP) by phosphofructokinase, and subsequently cleaved by FBP aldolase (FBPA) to 3-carbon molecules, or oxidized to 2-keto-3-deoxy-6-phosphogluconate (KDPG) and ultimately cleaved to 3-carbon sugars by the enzyme catalyzed by KDPG aldolase. One of those 3-carbon molecules is recycled back through the RuMP pathway and the other 3-carbon fragment is utilized for cell growth.

In the third phase (the "rearrangement" phase), the regeneration of 3 molecules of ribulose-5-phosphate is accomplished from the two remaining molecules of fructose-6-phosphate (from stage 1) and the one molecule of the 3-carbon sugar from stage 2. There are two possible routes to achieve the rearrangement. These routes in the rearrangement phase differ in that they involve either transaldolase (TA) or sedoheptu lose-1,7-bisphosphatase (SB Pase).

In methanotrophs and methylotrophs, the RuMP pathway may occur as one of three variants. These are the KDPGA/TA, FBPA/SBPase and FBPA/TA pathways. However, only two of these variants are commonly found. These two pathways are the FBPA/TA (fructose bisphophotase aldolase/Transaldolase) or the KDPGA/TA (keto deoxy phosphgogluconate aldolase/transaldolase) pathway, wherein only the FBPA/TA pathway is exergonic (Dijkhuizen et al. (1992) The Physiology and biochemistry of aerobic methanol-utilizing gram negative and gram positive bacteria. In: Methane and Methanol utilizers. P. 149-Colin Murrell and Howard Dalton, Plenum Press NY). Available literature suggests that obligatory methanotrophic bacteria such as *Methylomonas* rely solely on the KDPGA/ TA pathway (Entner-Douderoff Pathway), while facultative methylotrophs utilize either the FBPA/SBPase or the FBPA/ TA pathway (Dijkhuizen et al. supra). Energetically, this pathway is not as efficient as the Embden-Meyerhof pathway and thus could result in lower cellular production yields, as compared to organisms that do use the latter pathway. Therefore, a more energy efficient carbon processing pathway would greatly enhance the commercial viability of the methanotrophic platform for the generation of materials.

The problem to be solved therefore is to discover genes encoding a more energetically efficient carbon flux pathway that would enable a methanotrophic bacterial strain to better able to serve as a platform for the production of proteins and carbon containing materials. Applicants have solved the stated problem by providing the genes encoding the carbon flux pathway in a strain of *Methylomonas*. This pathway contains not only the expected elements of the Entner-Douderoff Pathway (including the 2-keto-3-deoxy-6-phosphogluconate aldolase) but additionally contains the elements of the more energy efficient Embden-Meyerhof pathway, containing the fructose-1,6-biphosphate aldolase. This discovery will permit the engineering of methanotrophs and other organisms for the energy efficient conversion of single carbon substrates such as methane and methanol to commercially useful products in the food and feed and materials industries.

SUMMARY OF THE INVENTION

The present invention provides an isolated nucleic acid molecule encoding a *Methylomonas* sp carbon flux enzyme, selected from the group consisting of:

(a) an isolated nucleic acid molecule encoding the amino acid sequence selected from the group consisting of SEQ ID NOs:2, 4, 6, 8, 10, 12, 14, 16, 18, and 20;

(b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and (c) an isolated nucleic acid molecule that is complementary to (a) or (b).

Additionally the invention provides the gene products, encoded by the present invention and chimera made from the instant genes by operably linking the instant genes to suitable regulatory sequences. Similarly the invention provides transformed host cells expressing the instant genes or their chimera.

The invention additionally provides a method of obtaining a nucleic acid fragment encoding a carbon flux enzyme comprising:

(a) probing a genomic library with the nucleic acid fragment of the present invention;

(b) identifying a DNA clone that hybridizes with the nucleic acid fragment of the present invention; and (c) sequencing the genomic fragment that comprises the clone identified in step (b), wherein the sequenced genomic fragment encodes a carbon flux enzyme.

Alternatively the invention provides a method of obtaining a nucleic acid fragment encoding a carbon flux enzyme comprising:

(a) synthesizing at least one oligonucleotide primer corresponding to a portion of the sequence selected from the group consisting of SEQ ID NO:1, 3, 5, 7, 9, 11, 13, 15, 17, and 19;

(b) amplifying an insert present in a cloning vector using the oligonucleotide primer of step (a);

wherein the amplified insert encodes a portion of an amino acid sequence encoding a carbon flux enzyme.

In another embodiment the invention provides a method of altering carbon flow through a methanotrophic bacteria comprising, over-expressing at least one carbon flux gene selected from the group consisting of SEQ ID NO:1, 3, 5, 7, 9, 11, 13, 15, 17 and 19 in a methanotrophic strain such that the carbon flow is altered through the strain.

Additionally the invention provides a mutated gene encoding a carbon flux enzyme having an altered biological activity produced by a method comprising the steps of:

(i) digesting a mixture of nucleotide sequences with restriction endonucleases wherein said mixture comprises:

a) a native carbon flux gene;

b) a first population of nucleotide fragments which will hybridize to said native carbon flux gene;

c) a second population of nucleotide fragments which will not hybridize to said native carbon flux gene;

wherein a mixture of restriction fragments are produced;

(ii) denaturing said mixture of restriction fragments;

(iii) incubating the denatured said mixture of restriction fragments of step (ii) with a polymerase;

(iv) repeating steps (ii) and (iii) wherein a mutated carbon flux gene is produced encoding a protein having an altered biological activity.

BRIEF DESCRIPTION OF THE DRAWINGS SEQUENCE DESCRIPTIONS AND BIOLOGICAL DEPOSITS

FIG. 1 is a schematic showing the enzyme catalyzed reaction of the Embden-Meyerhof and the Entner-Douderoff carbon pathways present in the *Methylomonas* 16a strain.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2), 345–373 (1984) which are herein incorporated by reference. The symbols and format used for nucleotide and amino acid sequence data comply with the rules set forth in 37 C.F.R. §1.822.

| Description | SEQ ID Nucleic acid | SEQ ID Peptide |
|---|---|---|
| Transaldolase: Carbon Flux | 1 | 2 |
| Transaldolase: Carbon Flux | 3 | 4 |
| Fructose bisphosphate aldoslase: Carbon Flux | 5 | 6 |
| Fructose bisphosphate aldoslase: Carbon Flux | 7 | 8 |
| KHG/KDPG Aldolase: Carbon Flux | 9 | 10 |
| Phosphoglucomutase: carbon Flux | 11 | 12 |
| Glucose 6 phosphate isomerase: Carbon flux | 13 | 14 |

-continued

| Description | SEQ ID Nucleic acid | SEQ ID Peptide |
|---|---|---|
| Phosphofructokinase pyrophosphate dependent: Carbon Flux | 15 | 16 |
| 6-Phosphogluconate dehydratase: Carbon flux | 17 | 18 |
| Glucose 6 phosphate 1 dehydrogenase: Carbon Flux | 19 | 20 |

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| Methylomonas 16a | ATCC PTA 2402 | Aug. 21, 2000 |

DETAILED DESCRIPTION OF THE INVENTION

The invention relates to genes encoding enzymes in the carbon flux pathway from a methanotrophic bacteria. The pathway contains genes encoding fructose-1,6-biphosphate aldolase (FBP aldolase) and a pyrophosphate dependent phosphofructokinase pyrophosphate which are indicative of the Embden-Meyerhof pathway typically not found in methanotrophs. The Embden-Meyerhof pathway is energetically more favorable than the carbon flux pathway typically associated with these organisms. Additionally the invention provides genes encoding elements of the Entner-Douderoff Pathway, which is typically found in methanotrophic bacteria. These genes include 6-Phosphogluconate dehydratase, a glucose-6-phosphate-1-dehydrogenase, and a 2-keto-3-deoxy-6-phosphogluconate aldolase. Common to both pathways are new genes encoding a transaldolase and a phosphoglucomutase. Knowledge of the sequence of the present genes will be useful for altering the carbon flow in methanotrophs and other bacteria resulting in more productive bacterial fermentation platforms for the production of chemicals and food and feed products.

In this disclosure, a number of terms and abbreviations are used. The following definitions are provided.

"Open reading frame" is abbreviated ORF.

"Polymerase chain reaction" is abbreviated PCR.

The term "a C1 carbon substrate" refers to any carbon-containing molecule that lacks a carbon-carbon bond. Examples are methane, methanol, formaldehyde, formic acid, methylated amines, methylated thiols.

The term "RuMP" is the abbreviation for ribulose monophosphate and the "RuMP pathway" refers to the set of enzymes found in methanotrophic bacteria responsible of the conversion of the methane monooxygenase product (methanol, formaldehyde) to three carbon moieties useful for energy production in the methanotroph.

The term "Embden-Meyerhof pathway" refers to the series of biochemical reactions for conversion of hexoses such as glucose and fructose to important cellular 3-carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerhof pathway are the phosphofructokinase and fructose 1,6 bisphosphate aldolase.

The term "Entner-Douderoff pathway" refers to a series of biochemical reactions for conversion of hexoses such as as glucose or fructose to the important 3-carbon cellular intermediates pyruvate and glyceraldehyde 3 phosphate, without any net production of biochemically useful energy. The key enzymes unique to the Entner-Douderoff pathway are the 6 phosphogluconate dehydratase and the ketodeoxyphosphogluconate aldolase.

The term "high growth methanotrophic bacterial strain" refers to a bacterium capable of growth with methane or methanol as the sole carbon and energy source and which possesses a functional Embden-Meyerhof carbon flux pathway resulting in yield of cell mass per gram of C1 substrate metabolized. The specific "high growth methanotrophic bacterial strain" described herein is referred to as "*Methylomonas* 16a" or "16a", which terms are used interchangeably.

The term "methanotroph" or "methanotrophic bacteria" will refer to a prokaryotic microorganism capable of utilizing methane as its primary carbon and energy source.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "carbon flux gene" will refer to any gene encoding an enzyme that functions to convert C1 substrates in methanotrophic bacteria to metabolically useful products. As used herein "carbon flux genes" will be those encoding a phosphoglucomutase, a transaldolase, a glucose-6-phosphate isomerase, a phosphofructokinase (pyrophosphate dependent), a 6-Phosphogluconate dehydratase, and a glucose 6 phosphate 1 dehydrogenase, as well as the distinctive fructose bisphosphate aldolase and keto deoxy phosphogluconate aldolase.

"Carbon Flux enzymes" will refer to the gene products of the carbon flux genes.

The term "transaldolase" will be abbrevaited "TA" and will refer to an enzyme that catalyzes the reaction of sedoheptulose 7-phosphate and D-glyceraldehyde 3-phosphate to give D-erythrose 4-phosphate and D-fructose 6-phosphate The term "fructose bisphosphate aldolase" will be abbreviated "FFBPA" and will refer to an enzyme that catalyzes the reaction of D-fructose 1,6-bisphosphate to give glycerone-phosphate and D-glyceraldehyde 3-phosphate.

The term "keto deoxy phosphogluconate aldolase" will be abbreviated "KDPGA" and will refer to an enzyme that catalyzes the reaction of 2-dehydro-3-deoxy-d-gluconate 6-phosphate to give pyruvate and D-glyceraldehyde 3-phosphate.

The term "phosphoglucomutase" and will refer to an enzyme that catalyzes the interconversion of glucose-6-phosphate to glucose-1-phosphate.

The term "glucose-6-phosphate isomerase" and will refer to an enzyme that catalyzes the conversion of fructose-6-phosphate to glucose-6-phosphate.

The term "phosphofructokinase" and will refer to an enzyme that catalyzes the conversion of fructose-6-phosphate to fructose-1,6-bisphosphate.

The term "6-phosphogluconate dehydratase" and will refer to an enzyme that catalyzes the conversion of 6-phosphogluconate to 2-keto-3-deoxy-6-phosphogluconate (KDPG).

The term "6-phosphogluconate-6-phosphate-1 dehydrogenase" and will refer to an enzyme that catalyzes the conversion of glucose-6-phosphate to 6-phosphogluconate.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:2, 4, 6, 8, and 10. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The invention provides genes and gene products involved in the carbon flux pathway of a *Methylomonas* sp. The invention alternatively provides methods of altering carbon flux in a methanotrophic bacteria comprising the up-regulation or down-regulation of carbon flux either by introducing the present genes into a host or by suppressing the expression of sequence homologs to the present genes.

Isolation of *Methylomonas* 16a

The original environmental sample containing *Methylomonas* 16a was obtained from pond sediment. The pond sediment was inoculated directly into a defined mineral medium under 25% methane in air. Methane was used as the sole source of carbon and energy. Growth was followed until the optical density at 660 nm was stable, whereupon the culture was transferred to fresh medium such that a 1:100 dilution was achieved. After 3 successive transfers with methane as the sole carbon and energy source, the culture was plated onto defined minimal medium agar and incubated under 25% methane in air. Many methanotrophic bacterial species were isolated in this manner. However, *Methylomonas* 16a was selected as the organism to study due to the rapid growth of colonies, large colony size, its ability to grow on minimal media, and pink pigmentation indicative of an active biosynthetic pathway for carotenoids.

Methanotrophs are classified into three metabolic groups ("Type I", "Type X" or "Type II") based on the mode of carbon incorporation, morphology, % GC content and the presence or absence of key specific enzymes. Example 4, Table 2 shows key traits determined for *Methylomonas* 16a in relation to the three major groupings of methanotrophs. The strain clearly falls into the Type I grouping based on every trait, with the exception of nitrogen fixation. Available literature suggests that these organisms do not fix nitrogen. Therefore, *Methylomonas* 16a appears to be unique in this aspect of nitrogen metabolism.

16SrRNA extracted from the strain was sequenced and compared to known 16SrRNAs from other microorganisms. The data showed 96% identity to sequences from *Methylomonas* sp. KSP III and *Methylomonas* sp. Strain LW13. Based on this evidence, as well as the other physiological traits described in Table 2, it was concluded that the strain was a member of the genus *Methylomonas*.

The present sequences have been identified by comparison of random cDNA sequences to the GenBank database using the BLAST algorithms well known to those skilled in the art. The nucleotide sequence of two genes encoding fructose bisphosphate aldolase (FFBPA) have been identified. The gene sequences for these genes are given in SEQ ID NO:5 and SEQ ID NO:7. The corresponding gene products are given in SEQ ID NO:6 and SEQ ID NO:8. Similarly, two genes encoding a transaldolase associated with the carbon flux pathway have been identified. These genes are set forth in SEQ ID NO:1 and SEQ ID NO:3. Their corresponding gene products are set forth in SEQ ID NO:2 and SEQ ID NO:4. Additionally a gene encoding a keto deoxy phosphogluconate aldolase (KDPGA) has been identified and is given in SEQ ID NO:9 and the deduced amino acid sequence of the gene product is given in SEQ ID NO:10.

Genes encoding a phosphoglucomutase have also been identified where the genes and the corresponding gene products are given as SEQ ID NOs:11 and 12, respectively. Similarly, genes and gene products have been identified encoding a glucose 6 phosphate isomerase where the genes and their corresponding gene products are given as SEQ ID NO:13 and 14, respectively. Genes encoding a phosphofructokinase have also been identified where the genes and gene products are given as SEQ ID NOs:15 and 16, respectively. A 6-phosphogluconate dehydratase encoding gene has been identified and the gene and gene product are given in SEQ ID NOs:17 and 18, respectively. Another carbon flux enzyme, 6-phosphogluconate 6 phosphate 1 dehydrogenase, has been identified and the gene and gene product is given in SEQ ID NOs:19 and 20, respectively.

Accordingly, the present invention provides a *Methylomonas* sp having a gene encoding a fructose bisphosphate aldolase (FBP aldolase), a keto deoxy phosphgogluconate/transaldolase (KDPG aldolase), a phosphoglucomutase, a glucose 6 phosphate isomerase, a phosphofructokinase, a 6-phosphogluconate dehydratase, and a 6-phosphogluconate-6-phosphate 1 dehydrogenase.

More specifically the present strain is recognized as having a gene encoding an transaldolase having about 78% identity at the amino acid level over length of 328 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.) to the sequence set forth in SEQ ID NO:2. More preferred amino acid fragments are at least about 80%–90% identical to the sequences herein. Most preferred are amino acid fragments that are at least 95% identical to the amino acid fragments reported herein. Similarly, preferred transaldolase encoding nucleic acid sequences corresponding to the instant seqeunces are those encoding active proteins and which are at least 80% identical to the nucleic acid sequences of reported herein. More preferred transaldolase nucleic acid fragments are at least 90% identical to the sequences herein. Most preferred are transaldolase nucleic acid fragments that are at least 95% identical to the nucleic acid fragments reported herein.

More specifically the present strain is recognized as having a gene encoding an transaldolase having about 50% identity at the amino acid level over length of 160 amino acids using a Smith-Waterman alignment algorithm (W. R. Pearson, supra) to the sequence set forth in SEQ ID NO:4. More preferred amino acid fragments are at least about 80%–90% identical to the sequences herein. Most preferred are amino acid fragments that are at least 95% identical to the amino acid fragments reported herein. Similarly, preferred transaldolase encoding nucleic acid sequences corresponding to the instant seqeunces are those encoding active proteins and which are at least 80% identical to the nucleic acid sequences of reported herein. More preferred transaldolase nucleic acid fragments are at least 90% identical to the sequences herein. Most preferred are transaldolase nucleic acid fragments that are at least 95% identical to the nucleic acid fragments reported herein.

Additionally the present strain is recognized as having a gene encoding an FBP aldolase having about 76% identity at the amino acid level over length of 335 amino acids using a Smith-Waterman alignment algorithm (W. R. Pearson, supra) to the sequence set forth in SEQ ID NO:6. More preferred amino acid fragments are at least about 80%–90% identical to the sequences herein. Most preferred are amino acid fragments that are at least 95% identical to the amino acid fragments reported herein. Similarly, preferred FBP aldolase encoding nucleic acid sequences corresponding to the instant seqeunces are those encoding active proteins and which are at least 80% identical to the nucleic acid sequences of reported herein. More preferred FBP aldolase nucleic acid fragments are at least 90% identical to the sequences herein. Most preferred are FBP aldolase nucleic acid fragments that are at least 95% identical to the nucleic acid fragments reported herein.

Additionally the present strain is recognized as having a gene encoding an FBP aldolase having about 40% identity at the amino acid level over length of 358 amino acids using a Smith-Waterman alignment algorithm (W. R. Pearson, supra) to the sequence set forth in SEQ ID NO:8. More preferred amino acid fragments are at least about 80%–90% identical to the sequences herein. Most preferred are amino acid fragments that are at least 95% identical to the amino acid fragments reported herein. Similarly, preferred FBP aldolase encoding nucleic acid sequences corresponding to the instant seqeunces are those encoding active proteins and which are at least 80% identical to the nucleic acid sequences of reported herein. More preferred FBP aldolase nucleic acid fragments are at least 90% identical to the sequences herein. Most preferred are FBP aldolase nucleic acid fragments that are at least 95% identical to the nucleic acid fragments reported herein.

Additionally the present strain is recognized as having a gene encoding an KDPG aldolase having about 59% identity at the amino acid level over length of 212 amino acids using a Smith-Waterman alignment algorithm (W. R. Pearson, supra) to the sequence set forth in SEQ ID NO:10. More preferred amino acid fragments are at least about 80%–90% identical to the sequences herein. Most preferred are amino acid fragments that are at least 95% identical to the amino acid fragments reported herein. Similarly, preferred KDPG aldolase encoding nucleic acid sequences corresponding to the instant seqeunces are those encoding active proteins and which are at least 80% identical to the nucleic acid sequences of reported herein. More preferred KDPG aldolase nucleic acid fragments are at least 90% identical to the sequences herein. Most preferred are KDPG aldolase nucleic acid fragments that are at least 95% identical to the nucleic acid fragments reported herein.

Additionally the present strain is recognized as having a gene encoding an phosphoglucomutase having about 65% identity at the amino acid level over length of 545 amino acids using a Smith-Waterman alignment algorithm (W. R. Pearson, supra) to the sequence set forth in SEQ ID NO:12. More preferred amino acid fragments are at least about 80%–90% identical to the sequences herein. Most preferred are amino acid fragments that are at least 95% identical to the amino acid fragments reported herein. Similarly, preferred phosphoglucomutase encoding nucleic acid sequences corresponding to the instant seqeunces are those encoding active proteins and which are at least 80% identical to the nucleic acid sequences of reported herein. More preferred phosphoglucomutase nucleic acid fragments are at least 90% identical to the sequences herein. Most preferred are phosphoglucomutase nucleic acid fragments that are at least 95% identical to the nucleic acid fragments reported herein.

Additionally the present strain is recognized as having a gene encoding an glucose-6-phosphate isomerase having about 64% identity at the amino acid level over length of 592 amino acids using a Smith-Waterman alignment algorithm (W. R. Pearson, supra) to the sequence set forth in SEQ ID NO:14. More preferred amino acid fragments are at least about 80%–90% identical to the sequences herein. Most preferred are amino acid fragments that are at least 95% identical to the amino acid fragments reported herein. Similarly, preferred glucose-6-phosphate isomerase encoding nucleic acid sequences corresponding to the instant seqeunces are those encoding active proteins and which are at least 80% identical to the nucleic acid sequences of reported herein. More preferred glucose-6-phosphate isomerase nucleic acid fragments are at least 90% identical to the sequences herein. Most preferred are glucose-6-phosphate isomerase nucleic acid fragments that are at least 95% identical to the nucleic acid fragments reported herein.

Additionally the present strain is recognized as having a gene encoding an phosphofructokinase having about 63% identity at the amino acid level over length of 437 amino acids using a Smith-Waterman alignment algorithm (W. R. Pearson, supra) to the sequence set forth in SEQ ID NO:16. More preferred amino acid fragments are at least about 80%–90% identical to the sequences herein. Most preferred are amino acid fragments that are at least 95% identical to the amino acid fragments reported herein. Similarly, preferred phosphofructokinase encoding nucleic acid sequences corresponding to the instant seqeunces are those encoding active proteins and which are at least 80% identical to the nucleic acid sequences of reported herein. More preferred phosphofructokinase nucleic acid fragments are at least 90% identical to the sequences herein. Most preferred are phosphofructokinase nucleic acid fragments that are at least 95% identical to the nucleic acid fragments reported herein.

Additionally the present strain is recognized as having a gene encoding an 6-phosphogluconate dehydratase having about 60% identity at the amino acid level over length of 618 amino acids using a Smith-Waterman alignment algorithm (W. R. Pearson, supra) to the sequence set forth in SEQ ID NO:18. More preferred amino acid fragments are at least about 80%–90% identical to the sequences herein. Most preferred are amino acid fragments that are at least 95% identical to the amino acid fragments reported herein. Similarly, preferred 6-phosphogluconate dehydratase encoding nucleic acid sequences corresponding to the instant seqeunces are those encoding active proteins and which are at least 80% identical to the nucleic acid sequences of reported herein. More preferred 6-phosphogluconate dehydratase nucleic acid fragments are at least 90% identical to the sequences herein. Most preferred are 6-phosphogluconate dehydratase nucleic acid fragments that are at least 95% identical to the nucleic acid fragments reported herein.

Additionally the present strain is recognized as having a gene encoding an encoding a 6-phosphogluconate-6-phosphate-1-dehydrogenase having about 58% identity at the amino acid level over length of 501 amino acids using a Smith-Waterman alignment algorithm (W. R. Pearson, supra) to the sequence set forth in SEQ ID NO:20. More preferred amino acid fragments are at least about 80%–90% identical to the sequences herein. Most preferred are amino acid fragments that are at least 95% identical to the amino acid fragments reported herein. Similarly, preferred 6-phosphogluconate-6-phosphate-1-dehydrogenase encoding nucleic acid sequences corresponding to the instant seqeunces are those encoding active proteins and which are at least 80% identical to the nucleic acid sequences of reported herein. More preferred 6-phosphogluconate-6-phosphate-1-dehydrogenase nucleic acid fragments are at least 90% identical to the sequences herein. Most preferred are 6-phosphogluconate-6-phosphate-1-dehydrogenase nucleic acid fragments that are at least 95% identical to the nucleic acid fragments reported herein.

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci. USA* 82, 1074, (1985)) or strand displacement amplification (SDA, Walker, et al., *Proc. Natl. Acad. Sci. U.S.A.*, 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.; Rychlik, W. (1993) In White, B. A. (ed.), *Methods in Molecular Biology*, Vol. 15, pages 31–39, PCR Protocols: Current Methods and Applications. Humania Press, Inc., Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Recombinant Expression—Microbial

The genes and gene products of the instant sequences may be produced in heterologous host cells, particularly in the cells of microbial hosts. Expression in recombinant microbial hosts may be useful for the expression of various pathway intermediates, for the modulation of pathways already existing in the host, and for the synthesis of new products heretofore not possible using the host. Additionally, the gene products may be useful for conferring higher growth yields of the host or for enabling alternative growth modes to be utilized.

Preferred heterologous host cells for expression of the instant genes and nucleic acid molecules are microbial hosts that can be found broadly within microbial families and which grow over a wide range of temperatures, pH values, and solvent tolerances. Such microbes will include generally bacteria, yeast, and filamentous fungi. Specifically, suitable yeasts and fungi will include, but are not limited to, *Aspergillus, Saccharomyces, Pichia, Candida*, and *Hansenula*. Suitable bacterial species include, but are not limited to, *Salmonella, Bacillus, Acinetobacter, Rhodococcus, Streptomyces, Escherichia*, and *Pseudomonas*. Most preferred hosts for the expression of the present carbon flux genes are members of the methanotrophic class of bacteria including *Methylomonas, Methylococcus* and *Methylobacter*. Particularly suited for transformation will be members of the genus *Methylomonas*. These bacterial species have the ability to convert single carbon substrates such as methane and methanol to useful products and these genes are particularly suited for substrates found in these hosts.

Of particular interest in the present invention are high growth obligate methanotrophs having an energetically favorable carbon flux pathway. For example, Applicants have discovered a specific strain of methanotroph having several pathway features which make it particularly useful for carbon flux manipulation. This type of strain has served as the host in the present application and is known as *Methylomonas* 16a (ATCC PTA 2402).

The present strain contains several anomalies in the carbon utilization pathway. For example, based on genome sequence data, the strain is shown to contain genes for two pathways of hexose metabolism. The Entner-Douderoff pathway which utilizes the keto-deoxy phosphogluconate aldolase enzyme is present in the strain. It is generally well accepted that this is the operative pathway in obligate methanotrophs. Also present, however, is the Embden-Meyerhof pathway which utilizes the fructose bisphosphate aldolase enzyme. It is well known that this pathway is either not present or not operative in obligate methanotrophs. Energetically, the latter pathway is most favorable and allows greater yield of biologically useful energy and ultimately production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate dependent instead of ATP dependent. This feature adds to the energy yield of the pathway by using pyrophosphate instead of ATP. Because of its significance in providing an energetic advantage to the strain this gene in the carbon flux pathway is considered diagnostic for the present strain.

Comparison of the pyrophosphate dependent phosphofructokinase gene sequence (SEQ ID NO: 15) and deduced amino acid sequence (SEQ ID NO:16) to public databases reveals that the most similar known sequences are about 63% identical to the amino acid sequence reported herein over a length of 437 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 80%–90% identical to the sequences herein. Most preferred are nucleic acid fragments that are at least 95% identical to the amino acid fragments reported herein. Similarly, preferred pyrophosphate dependent phosphofructokinase encoding nucleic acid sequences corresponding to the instant gene are those encoding active proteins and which are at least 80% identical to the nucleic acid sequences of reported herein. More preferred pyrophosphate dependent phosphofructokinase nucleic acid fragments are at least 90% identical to the sequences herein. Most preferred are pyrophosphate dependent phosphofructokinase nucleic acid fragments that are at least 95% identical to the nucleic acid fragments reported herein.

In methanotrophic bacteria methane is converted to biomolecules via a cyclic set of reactions known as the ribulose monophosphate pathway or RuMP cycle. This pathway is comprised of three phases, each phase being a series of enzymatic steps (FIG. 1). The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those three-carbon molecules is recycled back through the RuMP pathway and the other 3-carbon fragment is utilized for cell growth. In methanotrophs and methylotrophs the RuMP pathway may occur as one of three variants. However, only two of these variants are commonly found: the FBP/TA (fructose bisphosphotase/Transaldolase) or the KDPG/TA (keto deoxy phosphogluconate/transaldolase) pathway (Dijkhuizen L., G. E. Devries. The Physiology and biochemistry of aerobic methanol-utilizing gram negative and gram positive bacteria. In: Methane and Methanol Utilizers 1992, ed Colin Murrell and Howard Dalton Plenum Press NY).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected whereas the former is not. The finding of the FBP genes in an obligate methane utilizing bacterium is both surprising and suggestive of utility. The FBP pathway is energetically favorable to the host microorganism due to the fact that more energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane utilizing organisms as production platforms for either single cell protein or for any other product derived from the flow of carbon through the RuMP pathway.

Accordingly the present invention provides a method for altering carbon flux in a high growth, energetically favorable *Methylomonas* strain which (a) grows on a C1 carbon substrate selected from the group consisting of methane and methanol; and (b) comprises a functional Embden-Meyerhof carbon pathway, said pathway comprising a gene encoding a pyrophosphate dependent phosphofructokinase enzyme.

Microbial expression systems and expression vectors containing regulatory sequences that direct high level expression of foreign genes are well known to those skilled in the art. Any of these could be used to construct chimeric genes for expression of the any of the present genes. These chimeric genes could then be introduced into appropriate microorganisms via transformation to provide recombinant expression of the enzymes and manipulation of the carbon pathways.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Pathway Engineering

The present genes may be used to affect carbon flow in bacteria and specifically methanotrophic bacteria. Commercial applications of the methanotrops have revolved around the production of single cell protein (Villadsen, John, *Recent Trends Chem. React. Eng.*, [Proc. Int. Chem. React. Eng. Conf.], 2nd (1987), Volume 2, 320–33. Editor(s): Kulkarni, B. D.; Mashelkar, R. A.; Sharma, M. M. Publisher: Wiley East, New Delhi, India; Naguib, M., Proc. OAPEC Symp. Petroprotein, [Pap.] (1980), Meeting Date 1979, 253–77, Publisher: Organ. Arab Pet. Exporting Countries, Kuwait, Kuwait) and the epoxidation of alkenes for production of chemicals (U.S. Pat. No. 4,348,476). These C1 substrate utilizing bacteria also are known to produce polysaccharides, used as thickeners in food and non-food industries, and isoprenoid compounds and carotenoid pigments of various carbon lengths (Urakami et al., *J. Gen. Appl. Microbiol.* (1986), 32(4), 317–41). The production of all of these commercially useful products will be impacted by alterations in carbon flux, in general, and by manipulation of the present genes, in particular. Such manipulation may be effected by the up- or down-regulation of various members of the carbon flux pathway.

Many of the key genes in the carbon utilization pathway are now disclosed in the present invention. Referring to FIG. 1, for example, the present invention provides genes encoding two distinct carbon flux pathways isolated from a methanotrophic bacteria. The genes and gene products are set forth in SEQ ID NO:1-SEQ ID NO:20, and encode both a KDPG aldolase and a FBP aldolase as well as a phosphoglucomutase, pyrophosphate dependent phosphofructokinase pyrophosphate, 6-phosphogluconate dehydratase, and a glucose 6 phosphate 1 dehydrogenase. The phosphoglucomutase is responsible for the interconversion of glucose-6-phosphate to glucose-1-phosphate, which feeds into either the Entner douderoff or Embden-Meyerhof carbon flux pathways. As shown in FIG. 1, fructose-6-phosphate may be converted to either glucose-6-phosphase by glucose phophate isomerase (Entner-Douderoff) or to fructose-1,6-bisphosphate (FBP) by a phosphofructokinase (Embden-Meyerhof). Following the Embden-Meyerhof pathway, FBP is then taken to two three-carbon moieties, dihydroxyacetone and 3-phosphoglyceraldehyde by the FBP aldolase. Returning to the Entner-Douderoff pathway, glucose-6-phosphate is taken to 6-phosphogluconate by a glucose-6-phosphate dehydrogenase which is subsequently taken to 2-keto-3-deoxy-6-phosphogluconate (KDPG) by a 6 phosphogluconate dehydratase. The KDPG is then converted to two three-carbon moieties (pyruvate and 3-phosphoglyceraldehyde) by a KDPG aldolase. Thus, the Embden-Meyerhof and Entner-Douderoff pathways are rejoined at the level of 3-phosphoglyceraldehyde. Manipulations in any one or all of these genes may be used for commercial advantage in the production of materials from a variety of bacteria and most suitably from methanotrophic bacteria.

Methods of manipulating genetic pathways are common and well known in the art. Selected genes in a particularly pathway may be upregulated or down regulated by variety of methods. Additionally, competing pathways in the organism may be eliminated or sublimated by gene disruption and similar techniques.

Once a key genetic pathway has been identified and sequenced, specific genes may be upregulated to increase the output of the pathway. For example, additionally copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be lafter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Tyl element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Within the context of the present invention it may be useful to modulate the expression of the carbon flux pathway. It is apparent from the known pathways in methanotrophic bacteria that there can be utility in either the FBP/TA or KDGP/TA pathway, depending on the target product. The FBP/TA pathway is more energy-yielding and thus is advantageous from the standpoint of producing more cellular mass per unit of methane metabolized. Thus if the strain is forced to utilize this pathway via a gene knock-out of the KDGP/TA pathway, it is anticipated that greater cell mass will be produced. In addition, the production of chemicals that have a high energy requirement for biosynthesis in the form of ATP may also be enhanced by deletion or mutation of the KDGP/TA pathway. Chemical production requiring pyruvate as a key intermediate, however, might benefit from the deletion or knock-out of the FBP/TA pathway genes. As an integral part of the *Methylomonas* production platform it is desirable to have the capability to utilize either pathway via introduction of specialized regulatory gene promoters that will enable either pathway to be switched on or off in the presence of chemicals that could be added to the fermentation.

More specifically, it has been noted that the present *Methylomonas* 16a comprises genes encoding both the Entner-Douderoff and Embden-Meyerhof carbon flux pathways. Because the Embden-Meyerhof pathway is more energy efficient it may be desirable to over-express the genes in this pathway. Additionally, it is likely that the Entner-Douderoff pathway is a competitive pathway and inhibition of this pathway may lead to increased energy efficiency in the Embden-Meyerhof system. This might be accomplished by selectively using the above described methods of gene down regulation on the sequence encoding the keto-deoxy phosphogluconate aldolase (SEQ ID NO: 9) or any of the other members of the Entner-Ddouderoff system and upregulating the gene encoding the fructose bisphosphatase aldolase of the Embden-Meyerhof system (SEQ ID NO:5 OR 7). In this fashion, the carbon flux in the present *Methylomonas* 16a may be optimized. Additionally, where the present strain has been engineered to produce specific organic materials such as aromatics for monomer production, optimization of the carbon flux pathway will lead to increased yields of these materials.

Industrial Scale Production

Where the engineering of a commercial bacterial production platform comprising the present genes is desired, a variety of culture methodologies may be applied. For example, large scale production of a specific product or products from a recombinant microbial host may be produced by both batch or continuous culture methodologies A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial use of the instant gene pathways may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added and valuable products, by-products or waste products continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Protein Engineering

It is contemplated that the present nucleotide sequences may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp.1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605, 793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The carbon flux sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol. (Maniatis supra).

Gene Expression Profiling

The present carbon flux genes may be used in connection with gene expression profiling technology for metabolic characterization of the cell from which the genes came. For example, many external changes such as changes in growth condition or exposure to chemicals can cause induction or repression of genes in the cell. The induction or repression of genes can be used for a screening system to determine the best growth conditions for a production organism and drug discovery with similar mode of action compound, just to mention a few. On the other hand, by amplifying or disrupting genes, one can manipulate the production of the amount of cellular products as well as the timeline upon which those products are produced. All or a portion of the present nucleic acid fragments of the instant invention may be used as probes for gene expression monitoring and gene expression profiling.

For example, all or a portion of the instant nucleic acid fragments may be immobilized on a nylon membrane or a glass slide. A Generation II DNA spotter (Molecular Dynamics) is one of the available technologies to array the DNA samples onto the coated glass slides. Other array methods are also available and well known in the art. After the cells are grown in various growth conditions or treated with potential candidates, cellular RNA is purified. Fluorescent or radioactive labeled target cDNA can be made by reverse transcription of mRNA. The target mixture is hybridized to the probes and washed using conditions well known in the art. The amount of the target gene expression is quantified by the intensity of radioactivity or fluorescence labels (e.g., confocal laser microscope: Molecular Dynamics). The intensities of radioactivity or fluorescent label at the immobilized probes are measured using technology well known in the art. The two color fluorescence detection scheme (e.g., Cy3 and Cy5) has the advantage over radioactively labeled targets by allowing rapid and simultaneous differential expression analysis of independent samples. In addition, the use of ratio measurements compensates for probe to probe variation of intensity due to DNA concentration and hybridization efficiency. In the case of fluorescence labeling, the two fluorescent images obtained with the appropriate excitation and emission filters constitute the raw data from which differential gene expression ratio values are calculated. The intensity of images are analyzed using the available software (e.g., Array Vision 4.0: Imaging Research Inc.) well known in the art and normalized to compensate for the differential efficiencies of labeling and detection of the label. There are many different ways known in the art to normalize the signals. One of the ways to normalize the signal is by correcting the signal against internal controls. Another way is to run a separate array with labeled genomic driven DNA and compare the signal with mRNA driven signals. This method also allows measurement of the transcript abundance. The array data of individual genes is examined and evaluated to determine the induction or repression of each gene under the test conditions.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Besffit" programs were used the default gap creation penalty of 50 and the default gap extension penalty of 3 were used. In any cases where GCG program parameters were not prompted for, in these or any other GCG program, default values were used.

Multiple alignment of the sequences was performed using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.).

The meaning of abbreviations is as follows: "h" means hour(s), "min" means minute(s), "sec" means second(s), "d" means day(s), "mL" means milliliters, "L" means liters.

Example 1

Isolation Of *Methylomonas* 16a

The original environmental sample containing the isolate was obtained from pond sediment. The pond sediment was inoculated directly into a defined mineral medium under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto defined minimal medium agar and incubated under 25% methane in air. Many methanotrophic bacterial species were isolated in this manner. However, *Methylomonas* 16a was selected as the organism to study due to the rapid growth of colonies, large colony size, ability to grow on minimal media, and pink pigmentation indicative of an active biosynthetic pathway for carotenoids.

Example 2

Preparation of Genomic DNA for Sequencing and Segeunce Generation

Genomic DNA was isolated from *Methylomonas* 16a according to standard protocols.

Genomic DNA and library construction were prepared according to published protocols (Fraser et al The Minimal Gene Complement of *Mycoplasma genitalium*; Science 270, 1995). A cell pellet was resuspended in a solution containing 100 mM Na-EDTA pH 8.0, 10 mM tris-HCl pH 8.0, 400 mM NaCl, and 50 mM MgCl2.

Genomic DNA preparation After resuspension, the cells were gently lysed in 10% SDS, and incubated for 30 minutes at 55° C. After incubation at room temperature, proteinase K was added to 100 µg/ml and incubated at 37° C. until the suspension was clear. DNA was extracted twice with tris-equilibrated phenol and twice with chloroform. DNA was precipitated in 70% ethanol and resuspended in a solution containing 10 mM tris-HCl and 1 mM Na-EDTA (TE) pH 7.5. The DNA solution was treated with a mix of RNAases, then extracted twice with tris-equilibrated phenol and twice with chloroform. This was followed by precipitation in ethanol and resuspension in TE.

Library construction 200 to 500 µg of chromosomal DNA was resuspended in a solution of 300 mM sodium acetate, 10 mM tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised, cleaned and a two-step ligation procedure was used to produce a high titer library with greater than 99% single inserts.

Sequencing A shotgun sequencing strategy approach was adopted for the sequencing of the whole microbial genome (Fleischmann, Robert et al Whole-Genome Random sequencing and assembly of *Haemophilus influenzae* Rd Science, 269: 1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent coverage at least two times in both directions.

Example 3

Identification and Characterization of Bacteria ORF's

The carbon flux genes isolated from *Methylomonas* 16a were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. All comparisons were done using either the BLASTNnr or BLASTXnr algorithm. The results of the BLAST comparison is given in Table 1 which summarize the sequences to which they have the most similarity. Table 1 displays data based on the BLASTXnr algorithm with values reported in expect values. The Expect value estimates the statistical significance of the match, specifying the number of matches, with a given score, that are expected in a search of a database of this size absolutely by chance.

TABLE 1

Genes Characterized From Methylomonas 16a

| Gene Name | Similarity Identified | SEQ ID | SEQ ID Peptide | % Identity [a] | % Similarity [b] | E-value [c] | Citation |
|---|---|---|---|---|---|---|---|
| Transaldolase | Transaldolase GI:1729831 *Anabaena variabilis*. | 1 | 2 | 78% | 90% | 2.7e-92 | Kohler, U., et al., Plant Mol. Biol. 30 (1), 213–218 (1996) |
| MIPB-transaldolase | Transaldolase GI:7443254 *Escherichia coli* | 3 | 4 | 50% | 79% | 1e-23 | Blattner F.R. et. al Science 277:1453–1474 (1997). |
| FBA or FDA | Fructose bisphosphate aldolase | 5 | 6 | 76% | 92% | 4.1e-111 | Alefounder P.R. et. al. Mol. Microbiol. 3:723–732 (1989). |
| FBA or FDA | Fructose bisphosphate aldolase | 7 | 8 | 40% | 70% | 2.3e-39 | van den Bergh E.R. et al.; J. Bacteriol. 178:888–893 (1996). |
| KHG/KDPG Aldolase | (AL352972) KHG/KDPG aldolase *Streptomyces coelicolor* | 9 | 10 | 59% | 72% | 1e-64 | Redenbach et al., Mol. Microbiol. 21 (1), 77–96 (1996) |
| Phosphogluco-mutase | Phosphoglucomutase (Glucose Phosphomutase) (Pgm)>>gi\|3241933\|gb\|AAD03475.1\| | 11 | 12 | 65% | 85% | 1.7e-140 | Lepek et al., Direct Submission \|gb\|AAD03475.1\| |
| Glucose 6 phosphate isomerase | Glucose 6 phosphate isomerase gi\|396360\|gb\|AAC43119.1 | 13 | 14 | 64% | 81% | 1.6e-136 | Blattner et al., Nucleic Acids Res. 21 (23), 5408–5417 (1993) |

TABLE 1-continued

Genes Characterized From Methylomonas 16a

| Gene Name | Similarity Identified | SEQ ID | SEQ ID Peptide | % Identity [a] | % Similarity [b] | E-value [c] | Citation |
|---|---|---|---|---|---|---|---|
| Phosphofructo-kinase pyrophosphate dependent | Phosphofructokinase pyrophosphate dependent gi\|150931\|gb\|AAA25675.1\| (M67447) | 15 | 16 | 63% | 83% | 1.7e-97 | Ladror et al., J. Biol. Chem. 266, 16550–16555 (1991) |
| 6-Phospho-gluconate dehydratase | 6-Phosphogluconate dehydratase gi\|4210902\|gb\|AAD12045.1\| (AF045609) | 17 | 18 | 60% | 85% | 1.6e-141 | Willis et al., J. Bacteriol. 181 (14), 4176–4184 (1999) |
| Glucose 6 phosphate 1 dehydrogenase | Glucose 6 phosphate 1 dehydrogenase gi\|397854\|emb\|CAA52858.1\| (X74866) | 19 | 20 | 58% | 85% | 9.4e-123 | Hugouvieux-Cotte-Pattat, N, TITLE Direct Submission, gi\|397854\|emb\|CAA52858.1\| (X74866) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance

---

What is claimed is:

1. An isolated nucleic acid molecule encoding a fructose biphosphate aldolase enzyme, selected from the group consisting of:
   (a) an isolated nucleic acid molecule encoding the amino acid sequence as set forth in SEQ ID NO: 8, and
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
   an isolated nucleic acid molecule that is complementary to (a) or (b).

2. The isolated nucleic acid molecule of claim 1 as set forth in SEQ ID NO:7.

3. An isolated nucleic acid molecule comprising a first nucleotide sequence encoding a fructose biphosphate aldolase polypeptide that has at least 95% identity when compared to a polypeptide having the sequence as set forth in SEQ ID NO:8, or a second nucleotide sequence comprising the complement of the first nucleotide sequence.

4. A chimeric gene comprising the isolated nucleic acid fragment of claim 1 operably linked to suitable regulatory sequences.

5. A transformed host cell comprising a host cell and the chimeric gene of claim 4.

6. The transformed host cell of claim 5 wherein the host cell is selected from the group consisting of bacteria, yeast, and filamentous fungi.

7. The transformed host cell of claim 6 wherein the host cell is selected from the group consisting of *Aspergillus, Saceharomyces, Pichia, Candida, Hansenula, Salmonella, Bacillus, Acinetobacter, Rhodococcus, Streptomyces, Escherichia, Pseudomonas, Methylomonas, Methylocoecs* and *Methylobacter*.

* * * * *

SEQUENCE LISTING

<160> NUMBER OF SEQ ID NOS: 20

<210> SEQ ID NO 1
<211> LENGTH: 984
<212> TYPE: DNA
<213> ORGANISM: METHYLOMONAS SP.

<400> SEQUENCE: 1

```
atggcaagaa acttacttga gcaactccgc gagatgaccg ttgttgttgc cgataccggt     60
gacatccagg cgatcgaaac cttcaagccg cgcgatgcaa cgaccaaccc gtctttgatc    120
accgccgcgg cgcaaatgcc gcaatatcaa ggcatcgttg acgacacctt gaaaggtgcg    180
cgtgcgacgt tgggtgccag cgcttcggct gccgaggtgg cttcattggc gttcgatcgt    240
ttggcggttt ctttcggttt gaaaatcctg gaaatcatcg aaggtcgcgt ttccaccgag    300
gttgatgcgc gtttgtctta tgacaccgaa ggcactattg ccaaaggccg ggatctgatc    360
aaacaatacg aagctgcagg tgtttccaaa gagcgcgtac tgatcaaaat tgccgcgacc    420
tgggaaggca tccaggcggc tgccgttttg gaaaagaag gtattcacac caacttgacc    480
ctgttgttcg gtctgcacca ggcgattgct tgtgccgaaa acggcattac cctgatttct    540
ccgtttgtcg gccgtattct ggactggtac aaaaaagaca ctggccgcga ctcttatcct    600
tccaacgaag atcctggcgt attgtctgta actgaagttt ataactacta caaaaaattt    660
ggttataaaa ctgaagtcat gggcgcgagc ttccgtaaca tcggcgaaat caccgaattg    720
gcgggttgcg atctgttgac catcgcgcct tctctgctgg ccgaactgca atccgttgaa    780
ggtgatttgc cacgcaaact ggaccctgca aaagcagccg gttcttcgat cgaaaaaatc    840
agcgttgaca aagcgacttt cgagcgcatg cacgaagaaa accgcatggc caaagaaaaa    900
ctggccgaag gtatcgacgg ttttgcgaaa gcgttggaaa ccttggaaaa attgttggcg    960
gatcgtttgg ctgctctgga agca                                           984
```

<210> SEQ ID NO 2

-continued

```
<211> LENGTH: 328
<212> TYPE: PRT
<213> ORGANISM: METHYLOMONAS SP.

<400> SEQUENCE: 2
```

| | | | | | | | | | | | | | | | |
|---|---|---|---|---|---|---|---|---|---|---|---|---|---|---|---|
| Met | ala | Arg | Asn | Leu | Leu | Glu | Gln | Leu | Arg | Glu | Met | Thr | Val | Val | Val |
| 1 | | | | 5 | | | | | 10 | | | | | 15 | |
| Ala | Asp | Thr | Gly | Asp | Ile | Gln | Ala | Ile | Glu | Thr | Phe | Lys | Pro | Arg | Asp |
| | | | 20 | | | | | 25 | | | | | 30 | | |
| Ala | Thr | Thr | Asn | Pro | Ser | Leu | Ile | Thr | Ala | Ala | Gln | Met | Pro | Gln | |
| | | | 35 | | | | 40 | | | | | 45 | | | |
| Tyr | Gln | Gly | Ile | Val | Asp | Asp | Thr | Leu | Lys | Gly | Ala | Arg | Ala | Thr | Leu |
| | | 50 | | | | | 55 | | | | | 60 | | | |
| Gly | Ala | Ser | Ala | Ser | Ala | Ala | Glu | Val | Ala | Ser | Leu | Ala | Phe | Asp | Arg |
| 65 | | | | | 70 | | | | | 75 | | | | | 80 |
| Leu | Ala | Val | Ser | Phe | Gly | Leu | Lys | Ile | Leu | Glu | Ile | Ile | Glu | Gly | Arg |
| | | | | 85 | | | | | 90 | | | | | 95 | |
| Val | Ser | Thr | Glu | Val | Asp | Ala | Arg | Leu | Ser | Tyr | Asp | Thr | Glu | Gly | Thr |
| | | | 100 | | | | | 105 | | | | | 110 | | |
| Ile | Ala | Lys | Gly | Arg | Asp | Leu | Ile | Lys | Gln | Tyr | Glu | Ala | Ala | Gly | Val |
| | | | 115 | | | | | 120 | | | | | 125 | | |
| Ser | Lys | Glu | Arg | Val | Leu | Ile | Lys | Ile | Ala | Ala | Thr | Trp | Glu | Gly | Ile |
| | 130 | | | | | 135 | | | | | 140 | | | | |
| Gln | Ala | Ala | Val | Leu | Glu | Lys | Glu | Gly | Ile | His | Thr | Asn | Leu | Thr | |
| 145 | | | | | 150 | | | | | 155 | | | | | 160 |
| Leu | Leu | Phe | Gly | Leu | His | Gln | Ala | Ile | Ala | Cys | Ala | Glu | Asn | Gly | Ile |
| | | | | 165 | | | | | 170 | | | | | 175 | |
| Thr | Leu | Ile | Ser | Pro | Phe | Val | Gly | Arg | Ile | Leu | Asp | Trp | Tyr | Lys | Lys |
| | | | 180 | | | | | 185 | | | | | 190 | | |
| Asp | Thr | Gly | Arg | Asp | Ser | Tyr | Pro | Ser | Asn | Glu | Asp | Pro | Gly | Val | Leu |
| | | | 195 | | | | | 200 | | | | | 205 | | |
| Ser | Val | Thr | Glu | Val | Tyr | Asn | Tyr | Tyr | Lys | Lys | Phe | Gly | Tyr | Lys | Thr |
| | 210 | | | | | 215 | | | | | 220 | | | | |
| Glu | Val | Met | Gly | Ala | Ser | Phe | Arg | Asn | Ile | Gly | Glu | Ile | Thr | Glu | Leu |
| 225 | | | | | 230 | | | | | 235 | | | | | 240 |
| Ala | Gly | Cys | Asp | Leu | Leu | Thr | Ile | Ala | Pro | Ser | Leu | Leu | Ala | Glu | Leu |
| | | | | 245 | | | | | 250 | | | | | 255 | |
| Gln | Ser | Val | Glu | Gly | Asp | Leu | Pro | Arg | Lys | Leu | Asp | Pro | Ala | Lys | Ala |
| | | | 260 | | | | | 265 | | | | | 270 | | |
| Ala | Gly | Ser | Ser | Ile | Glu | Lys | Ile | Ser | Val | Asp | Lys | Ala | Thr | Phe | Glu |
| | | 275 | | | | | 280 | | | | | 285 | | | |
| Arg | Met | His | Glu | Glu | Asn | Arg | Met | ala | Lys | Glu | Lys | Leu | Ala | Glu | Gly |
| | 290 | | | | | 295 | | | | | 300 | | | | |
| Ile | Asp | Gly | Phe | Ala | Lys | Ala | Leu | Glu | Thr | Leu | Glu | Lys | Leu | Leu | Ala |
| 305 | | | | | 310 | | | | | 315 | | | | | 320 |
| Asp | Arg | Leu | Ala | Ala | Leu | Glu | Ala | | | | | | | | |
| | | | | 325 | | | | | | | | | | | |

```
<210> SEQ ID NO 3
<211> LENGTH: 480
<212> TYPE: DNA
<213> ORGANISM: METHYLOMONAS SP.

<400> SEQUENCE: 3
atggccgcgg gcggcgtggg cttgacgcaa ttgctgccag aactggccga agctattggt    60
```

-continued

| | |
|---|---|
| ccgacgagcc gatttcatgt gcaggtcatt ggtgacacgg tggaggacat cgttgcggaa | 120 |
| gccaaacggc tacacgattt gcccgtcgac atagtggtga aaattccggc gcatggcgcc | 180 |
| ggactggcgg ccatcaagca gatcaagcgc acgatattc cggtgctggc gacagcgatt | 240 |
| tacaacgtgc agcaaggttg gctggcggct ttgaacggcg ccgattatct ggcgccttat | 300 |
| ctgaatcgcg tcgataacca gggttttgac ggtattggcg tggtcgccga tctgcagagc | 360 |
| ttgatcgacc ggtatcaaat gcccaccaaa ctcctggtag cgagcttcaa aaacgtacaa | 420 |
| caggtgctgc aggtgttgaa actgggcgtg gcgtcggtga cgctgccttt ggacattgtg | 480 |

<210> SEQ ID NO 4
<211> LENGTH: 160
<212> TYPE: PRT
<213> ORGANISM: METHYLOMONAS SP.

<400> SEQUENCE: 4

```
Met Ala Ala Gly Gly Val Gly Leu Thr Gln Leu Leu Pro Glu Leu Ala
 1               5                  10                  15
Glu Ala Ile Gly Pro Thr Ser Arg Phe His Val Gln Val Ile Gly Asp
            20                  25                  30
Thr Val Glu Asp Ile Val Ala Glu Ala Lys Arg Leu His Asp Leu Pro
        35                  40                  45
Val Asp Ile Val Val Lys Ile Pro Ala His Gly Ala Gly Leu Ala Ala
    50                  55                  60
Ile Lys Gln Ile Lys Arg His Asp Ile Pro Val Leu Ala Thr Ala Ile
65                  70                  75                  80
Tyr Asn Val Gln Gln Gly Trp Leu Ala Ala Leu Asn Gly Ala Asp Tyr
                85                  90                  95
Leu Ala Pro Tyr Leu Asn Arg Val Asp Asn Gln Gly Phe Asp Gly Ile
            100                 105                 110
Gly Val Val Ala Asp Leu Gln Ser Leu Ile Asp Arg Tyr Gln Met Pro
        115                 120                 125
Thr Lys Leu Leu Val Ala Ser Phe Lys Asn Val Gln Gln Val Leu Gln
    130                 135                 140
Val Leu Lys Leu Gly Val Ala Ser Val Thr Leu Pro Leu Asp Ile Val
145                 150                 155                 160
```

<210> SEQ ID NO 5
<211> LENGTH: 1005
<212> TYPE: DNA
<213> ORGANISM: METHYLOMONAS SP.

<400> SEQUENCE: 5

| | |
|---|---|
| atggctttag tgtcattgcg acaacttttg gattatgcgg ccgagcatgg ctttgccgtg | 60 |
| ccggcgttca acgtcagcaa catggagcag gtacaggcca tcatgcaggc ggccgctgcc | 120 |
| tgcgatagtc cagtgatcat gcaaggttcg gccggcgcca accgctatgc cggcgaagtg | 180 |
| tttctacggc atttgatatt ggcggccgtg gagcaatatc cgcatattcc ggtcgtcatg | 240 |
| caccgcgacc atgcacccac gcccgacatc tgcgcgcaag ccatacaatc gggcttcagc | 300 |
| tcggtgatga tggacggttc gttgctggca gacatgaaaa ccccggcttc ttttgcatac | 360 |
| aacgtcgacg tcacccgcac cgtggtcaag atgcgcatg cctgcggcgt atcggtggaa | 420 |
| ggcgaaatcg gctgcctggg agcgctggag gccaagtccg cgcaagatca cagccgtttg | 480 |
| ctgaccgatc ccgacgaagc ggtcgaattc gtcgaacaga cccaggtcga tgccgtggcc | 540 |
| gtggccatcg gcaccagcca cggcgcctat aaattcagca agccgcccac cggcgaagtg | 600 |

```
ctggtgatca gtcgattgaa agaactgcag caacgactgc caaataccca ttttgtgatg    660
catggctcca gttcggtgcc gcaggattgg ttgaaaatca tcaacgatta tggcggcgat    720
attccggaaa cctatggcgt gccggtcgaa gaaatcgtcg aaggcataaa atatggtgtg    780
cgcaaggtca acatcgatac cgacctgcgc atggcgtcca ccggcgcgat gcgcaggttt    840
ctggcccaac cggaaaacgc ctcggagcta cacgcgcgca agacctatca agccgccagg    900
gacgcaatgc aggcattatg ccaggctcgc tacgaagcgt tcggttcggc gggacatgcc    960
ggcaaaatca aaccggtttc actggcggca atggccaaac gctat               1005
```

<210> SEQ ID NO 6
<211> LENGTH: 335
<212> TYPE: PRT
<213> ORGANISM: METHYLOMONAS SP.

<400> SEQUENCE: 6

```
Met ala Leu Val Ser Leu Arg Gln Leu Leu Asp Tyr Ala Ala Glu His
  1               5                  10                  15

Gly Phe Ala Val Pro Ala Phe Asn Val Ser Asn Met Glu Gln Val Gln
             20                  25                  30

Ala Ile Met Gln Ala Ala Ala Cys Asp Ser Pro Val Ile Met Gln
         35                  40                  45

Gly Ser Ala Gly Ala Asn Arg Tyr Ala Gly Glu Val Phe Leu Arg His
     50                  55                  60

Leu Ile Leu Ala Ala Val Glu Gln Tyr Pro His Ile Pro Val Val Met
 65                  70                  75                  80

His Arg Asp His Ala Pro Thr Pro Asp Ile Cys Ala Gln Ala Ile Gln
                 85                  90                  95

Ser Gly Phe Ser Ser Val Met Met Asp Gly Ser Leu Leu Ala Asp Met
            100                 105                 110

Lys Thr Pro Ala Ser Phe Ala Tyr Asn Val Asp Val Thr Arg Thr Val
        115                 120                 125

Val Lys Met ala His Ala Cys Gly Val Ser Val Glu Gly Glu Ile Gly
    130                 135                 140

Cys Leu Gly Ala Leu Glu Ala Lys Ser Ala Gln Asp His Ser Arg Leu
145                 150                 155                 160

Leu Thr Asp Pro Asp Glu Ala Val Glu Phe Val Glu Gln Thr Gln Val
                165                 170                 175

Asp Ala Val Ala Val Ala Ile Gly Thr Ser His Gly Ala Tyr Lys Phe
            180                 185                 190

Ser Lys Pro Pro Thr Gly Glu Val Leu Val Ile Ser Arg Leu Lys Glu
        195                 200                 205

Leu Gln Gln Arg Leu Pro Asn Thr His Phe Val Met His Gly Ser Ser
    210                 215                 220

Ser Val Pro Gln Asp Trp Leu Lys Ile Ile Asn Asp Tyr Gly Gly Asp
225                 230                 235                 240

Ile Pro Glu Thr Tyr Gly Val Pro Val Glu Glu Ile Val Glu Gly Ile
                245                 250                 255

Lys Tyr Gly Val Arg Lys Val Asn Ile Asp Thr Asp Leu Arg Met ala
            260                 265                 270

Ser Thr Gly Ala Met Arg Arg Phe Leu Ala Gln Pro Glu Asn Ala Ser
        275                 280                 285

Glu Leu Asp Ala Arg Lys Thr Tyr Gln Ala Ala Arg Asp Ala Met Gln
    290                 295                 300
```

```
Ala Leu Cys Gln Ala Arg Tyr Glu Ala Phe Gly Ser Ala Gly His Ala
305                 310                 315                 320

Gly Lys Ile Lys Pro Val Ser Leu Ala Ala Met ala Lys Arg Tyr
                325                 330                 335

<210> SEQ ID NO 7
<211> LENGTH: 1074
<212> TYPE: DNA
<213> ORGANISM: METHYLOMONAS SP.

<400> SEQUENCE: 7
atgacaaaaa tcttagatgt tgtaaaaccc ggcgttgtca ccggtgaaga tgtgcaaaaa      60 atttcgcaa  tctgcaaaga aaacaacttt gccttgccag ccgtcaacgt gatcagtacc     120
gataccatta atgcggtatt ggaagcggcc gccaaagcca aatcacctgt tgttatccag     180
ttttcaaatg gcggcgcggc tttcgttgcc ggtaaaggtt tgaaattgga aggtcaaggc     240
tgttcgattc atggtgccat ttcaggtgct caccacgttc accgcttggc ggaactctat     300
ggtgtacctg tcgttctgca taccgaccac gcggcgaaaa aattgctgcc atgggtagat     360
ggtatgctgg atgaaggtga aaaattcttt gcggccaccg gcaagccttt gttcagctcg     420
cacatgctgg acttgtccga agagagcctg aagaaaaaca tcgaaatctg cggtaaatac     480
ttggcgcgca tggcgaaaat gggtatgacc ttggaaatcg aactgggctg caccggcggt     540
gaagaagacg gcgtggacaa cagcggcatg gatcattccg cgttgtacac ccagccggaa     600
gacgtggctt acgcgtatga gcacctgagc aaaatcagcc ctaacttcac gattgcggct     660
tctttcggca acgtgcacgg cgtttactcg ccaggaaacg tcaagctgac gccaaaaatt     720
ctggataact cgcaaaaata cgtatccgaa aaattcggct tgccagctaa atcattgacc     780
ttcgtattcc atggcggctc tggttcgtct ccggaagaaa tcaaggaatc catcagctat     840
ggcgtagtga aaatgaacat cgataccgat acccaatggg caacctggga aggcgtgatg     900
aacttctaca gaaaaacga aggctatctg caaggccaga tcggcaatcc ggaaggtgcc     960
gacaagccga acaaaaaata ctatgaccca cgcgtatggc aacgtgccgg ccaagaaggc    1020
atggttgcac gtctgcaaca agcattccag gaattgaatg cagtaaacac gctg          1074

<210> SEQ ID NO 8
<211> LENGTH: 358
<212> TYPE: PRT
<213> ORGANISM: METHYLOMONAS SP.

<400> SEQUENCE: 8

Met Thr Lys Ile Leu Asp Val Val Lys Pro Gly Val Val Thr Gly Glu
  1               5                  10                  15

Asp Val Gln Lys Ile Phe Ala Ile Cys Lys Glu Asn Asn Phe Ala Leu
                 20                  25                  30

Pro Ala Val Asn Val Ile Ser Thr Asp Thr Ile Asn Ala Val Leu Glu
             35                  40                  45

Ala Ala Ala Lys Ala Lys Ser Pro Val Val Ile Gln Phe Ser Asn Gly
         50                  55                  60

Gly Ala Ala Phe Val Ala Gly Lys Gly Leu Lys Leu Glu Gly Gln Gly
 65                  70                  75                  80

Cys Ser Ile His Gly Ala Ile Ser Gly Ala His His Val His Arg Leu
                 85                  90                  95

Ala Glu Leu Tyr Gly Val Pro Val Val Leu His Thr Asp His Ala Ala
                100                 105                 110
```

-continued

```
Lys Lys Leu Leu Pro Trp Val Asp Gly Met Leu Asp Glu Gly Glu Lys
        115                 120                 125

Phe Phe Ala Ala Thr Gly Lys Pro Leu Phe Ser Ser His Met Leu Asp
    130                 135                 140

Leu Ser Glu Glu Ser Leu Glu Glu Asn Ile Glu Ile Cys Gly Lys Tyr
145                 150                 155                 160

Leu Ala Arg Met ala Lys Met Gly Met Thr Leu Glu Ile Glu Leu Gly
                165                 170                 175

Cys Thr Gly Gly Glu Glu Asp Gly Val Asp Asn Ser Gly Met Asp His
            180                 185                 190

Ser Ala Leu Tyr Thr Gln Pro Glu Asp Val Ala Tyr Ala Tyr Glu His
        195                 200                 205

Leu Ser Lys Ile Ser Pro Asn Phe Thr Ile Ala Ala Ser Phe Gly Asn
    210                 215                 220

Val His Gly Val Tyr Ser Pro Gly Asn Val Lys Leu Thr Pro Lys Ile
225                 230                 235                 240

Leu Asp Asn Ser Gln Lys Tyr Val Ser Glu Lys Phe Gly Leu Pro Ala
                245                 250                 255

Lys Ser Leu Thr Phe Val Phe His Gly Ser Gly Ser Ser Pro Glu
            260                 265                 270

Glu Ile Lys Glu Ser Ile Ser Tyr Gly Val Val Lys Met Asn Ile Asp
        275                 280                 285

Thr Asp Thr Gln Trp Ala Thr Trp Glu Gly Val Met Asn Phe Tyr Lys
    290                 295                 300

Lys Asn Glu Gly Tyr Leu Gln Gly Gln Ile Gly Asn Pro Glu Gly Ala
305                 310                 315                 320

Asp Lys Pro Asn Lys Lys Tyr Tyr Asp Pro Arg Val Trp Gln Arg Ala
                325                 330                 335

Gly Gln Glu Gly Met Val Ala Arg Leu Gln Gln Ala Phe Gln Glu Leu
            340                 345                 350

Asn Ala Val Asn Thr Leu
        355
```

<210> SEQ ID NO 9
<211> LENGTH: 636
<212> TYPE: DNA
<213> ORGANISM: METHYLOMONAS SP.

<400> SEQUENCE: 9

| | | | | | |
|---|---|---|---|---|---|
| gaaaatacta | tgtccgtcac | catcaaagaa | gtcatgacca | cctcgcccgt | tatgccggtc | 60 |
| atggtcatca | atcatctgga | acatgccgtc | cctctggctc | gcgcgctagt | cgacggtggc | 120 |
| ttgaaagttt | tggagatcac | attgcgcacg | ccggtggcac | tggaatgtat | ccgacgtatc | 180 |
| aaagccgaag | taccggacgc | catcgtcggc | gcgggcacca | tcatcaaccc | tcataccttg | 240 |
| tatcaagcga | ttgacgccgg | tgcggaattc | atcgtcagcc | ccggcatcac | cgaaaatcta | 300 |
| ctcaacgaag | cgctagcatc | cggcgtgcct | atcctgcccg | cgtcatcac | acccagcgag | 360 |
| gtcatgcgtt | tattggaaaa | aggcatcaat | gcgatgaaat | tctttccggc | tgaagccgcc | 420 |
| ggcggcatac | cgatgctgaa | atcccttggc | ggccccttgc | cgcaagtcac | cttctgtccg | 480 |
| accggcggcg | tcaatcccaa | aaacgcgccc | gaatatctgg | cattgaaaaa | tgtcgcctgc | 540 |
| gtcggcggct | cctggatggc | gccggccgat | ctggtagatg | ccgaagactg | gcggaaatc | 600 |
| acgcggcggg | cgagcgaggc | cgcggcattg | aaaaaa | | | 636 |

-continued

```
<210> SEQ ID NO 10
<211> LENGTH: 212
<212> TYPE: PRT
<213> ORGANISM: METHYLOMONAS SP.

<400> SEQUENCE: 10

Glu Asn Thr Met Ser Val Thr Ile Lys Glu Val Met Thr Thr Ser Pro
  1               5                  10                  15

Val Met Pro Val Met Val Ile Asn His Leu Glu His Ala Val Pro Leu
             20                  25                  30

Ala Arg Ala Leu Val Asp Gly Gly Leu Lys Val Leu Glu Ile Thr Leu
         35                  40                  45

Arg Thr Pro Val Ala Leu Glu Cys Ile Arg Arg Ile Lys Ala Glu Val
     50                  55                  60

Pro Asp Ala Ile Val Gly Ala Gly Thr Ile Ile Asn Pro His Thr Leu
 65                  70                  75                  80

Tyr Gln Ala Ile Asp Ala Gly Ala Glu Phe Ile Val Ser Pro Gly Ile
                 85                  90                  95

Thr Glu Asn Leu Leu Asn Glu Ala Leu Ala Ser Gly Val Pro Ile Leu
            100                 105                 110

Pro Gly Val Ile Thr Pro Ser Glu Val Met Arg Leu Leu Glu Lys Gly
        115                 120                 125

Ile Asn Ala Met Lys Phe Phe Pro Ala Glu Ala Ala Gly Gly Ile Pro
    130                 135                 140

Met Leu Lys Ser Leu Gly Gly Pro Leu Pro Gln Val Thr Phe Cys Pro
145                 150                 155                 160

Thr Gly Gly Val Asn Pro Lys Asn Ala Pro Glu Tyr Leu Ala Leu Lys
                165                 170                 175

Asn Val Ala Cys Val Gly Gly Ser Trp Met ala Pro Ala Asp Leu Val
            180                 185                 190

Asp Ala Glu Asp Trp Ala Glu Ile Thr Arg Arg Ala Ser Glu Ala Ala
        195                 200                 205

Ala Leu Lys Lys
    210

<210> SEQ ID NO 11
<211> LENGTH: 1434
<212> TYPE: DNA
<213> ORGANISM: METHYLOMONAS SP.

<400> SEQUENCE: 11
aacatgcaaa taaaaaccta taagaccaca ccctatgatg atcaaaaacc cggcacatcc      60
gggctaagaa aaaggttaa agttttttcag caatccggct atctggaaaa tttcgttcag     120
tccattttca atagtttaga agattttcag ggaaaaattc tagttttagg cggcgacggc     180
cgatatttta atcgacaagc gattcagatc atcatcaaaa tggcggccgc taacgggttt     240
ggtgagctga tcatcggcca gggcggtctg ttgtcgacac cggcggcctc caatgtcatc     300
cgcaaatatc gcgctttcgg cggcatcatt ctatccgcca gccacaatcc cggtggtccc     360
gacgaagact tcggcatcaa atataacgtc ggcaatggcg ggccggcacc ggaaaagttc     420
accgacgcct tgttcgaaaa cagcaaaaacc atcaccagct atcagatggc cgaaatcgac     480
gacatcgatc tcgatagcgt cggcgacgtc caaatcgatg gcataacaat ccgcatcatc     540
gatcccgtgg ccgattacgc cgaattgatg gcccggattt tcgatttcga cctgatcaag     600
caaagcatcg ccgccggctt gattaccttg cgcttcgacg cgatgcatgc cattaccggc     660
```

-continued

```
ccctatgcca aacatatact cgaagacgtg ctgggcgccg cgcccggttc ggtattcaac    720
gccgtaccgc tggaagactt cggcggcggc catcccgatc ccaacatggc gcacgcgcac    780
gagctcaccg aaatcatgtt cgggccgaat ccgccggttt tcggcgcggc ctcggacggt    840
gacggcgacc gcaacatgat catgggcgcc aatattttcg tcaccccag cgacagtctg     900 gccatcatgg cggccaacgc gcaattgatt cccgcctatg ccaagggcat tagcggcgtc    960
gcccgctcga tgccgaccag ccaggcggtc gacagggtcg cggataaatt gagtctgccg   1020
tgctacgaaa cgccgaccgg ctggaaattc tttggcaatt tgctggatgc cgacaaaatc   1080
acgctgtgcg gcgaagaaag cttcggttcc ggttccaatc atgtccggga aaagacggc    1140 ttgtgggccg tttattttg gctgaatttg cttgcgcgca agcgtcaacc ggccgaggat    1200
atcgtgcgtg aacattggca aaatacggc gcgacatct attgccgcca tgattacgaa     1260
gccgtcgatg ccgacatcgc caacggcatc gtagagcagc tgcgaaacca attgccgagc   1320
ttgcccggca aaacctgggg cgattacagc gtcaaattcg ccgacgaatt cagctatacc   1380
gatccggtcg atggtagcgt cagcagcaac caaggcatcc gcgtcggttt cgcc          1434
```

<210> SEQ ID NO 12
<211> LENGTH: 545
<212> TYPE: PRT
<213> ORGANISM: METHYLOMONAS SP.

<400> SEQUENCE: 12

```
Asn Met Gln Ile Lys Thr Tyr Lys Thr Thr Pro Tyr Asp Asp Gln Lys
  1               5                  10                  15

Pro Gly Thr Ser Gly Leu Arg Lys Lys Val Lys Val Phe Gln Gln Ser
             20                  25                  30

Gly Tyr Leu Glu Asn Phe Val Gln Ser Ile Phe Asn Ser Leu Glu Asp
         35                  40                  45

Phe Gln Gly Lys Ile Leu Val Leu Gly Gly Asp Gly Arg Tyr Phe Asn
     50                  55                  60

Arg Gln Ala Ile Gln Ile Ile Lys Met ala Ala Ala Asn Gly Phe
 65                  70                  75                  80

Gly Glu Leu Ile Ile Gly Gln Gly Gly Leu Leu Ser Thr Pro Ala Ala
                 85                  90                  95

Ser Asn Val Ile Arg Lys Tyr Arg Ala Phe Gly Ile Ile Leu Ser
            100                 105                 110

Ala Ser His Asn Pro Gly Gly Pro Asp Glu Asp Phe Gly Ile Lys Tyr
        115                 120                 125

Asn Val Gly Asn Gly Gly Pro Ala Pro Glu Lys Phe Thr Asp Ala Leu
    130                 135                 140

Phe Glu Asn Ser Lys Thr Ile Thr Ser Tyr Gln Met ala Glu Ile Asp
145                 150                 155                 160

Asp Ile Asp Leu Asp Ser Val Gly Asp Val Gln Ile Asp Gly Ile Thr
                165                 170                 175

Ile Arg Ile Ile Asp Pro Val Ala Asp Tyr Ala Glu Leu Met ala Arg
            180                 185                 190

Ile Phe Asp Phe Asp Leu Ile Lys Gln Ser Ile Ala Ala Gly Leu Ile
        195                 200                 205

Thr Leu Arg Phe Asp Ala Met His Ala Ile Thr Gly Pro Tyr Ala Lys
    210                 215                 220

His Ile Leu Glu Asp Val Leu Gly Ala Ala Pro Gly Ser Val Phe Asn
225                 230                 235                 240
```

```
Ala Val Pro Leu Glu Asp Phe Gly Gly His Pro Asp Pro Asn Met
            245                 250                 255
Ala His Ala His Glu Leu Thr Glu Ile Met Phe Gly Pro Asn Pro Pro
        260                 265                 270
Val Phe Gly Ala Ala Ser Asp Gly Asp Gly Asp Arg Asn Met Ile Met
            275                 280                 285
Gly Ala Asn Ile Phe Val Thr Pro Ser Asp Ser Leu Ala Ile Met ala
        290                 295                 300
Ala Asn Ala Gln Leu Ile Pro Ala Tyr Ala Lys Gly Ile Ser Gly Val
305                 310                 315                 320
Ala Arg Ser Met Pro Thr Ser Gln Ala Val Asp Arg Val Ala Asp Lys
                325                 330                 335
Leu Ser Leu Pro Cys Tyr Glu Thr Pro Thr Gly Trp Lys Phe Phe Gly
            340                 345                 350
Asn Leu Leu Asp Ala Asp Lys Ile Thr Leu Cys Gly Glu Glu Ser Phe
        355                 360                 365
Gly Ser Gly Ser Asn His Val Arg Glu Lys Asp Gly Leu Trp Ala Val
        370                 375                 380
Leu Phe Trp Leu Asn Leu Leu Ala Arg Lys Arg Gln Pro Ala Glu Asp
385                 390                 395                 400
Ile Val Arg Glu His Trp Gln Lys Tyr Gly Arg Asp Ile Tyr Cys Arg
                405                 410                 415
His Asp Tyr Glu Ala Val Asp Ala Asp Ile Ala Asn Gly Ile Val Glu
            420                 425                 430
Gln Leu Arg Asn Gln Leu Pro Ser Leu Pro Gly Lys Thr Trp Gly Asp
        435                 440                 445
Tyr Ser Val Lys Phe Ala Asp Glu Phe Ser Tyr Thr Asp Pro Val Asp
450                 455                 460
Gly Ser Val Ser Ser Asn Gln Gly Ile Arg Val Gly Phe Ala Asn Gly
465                 470                 475                 480
Ser Arg Ile Val Phe Arg Leu Ser Gly Thr Gly Thr Val Gly Ala Thr
                485                 490                 495
Leu Arg Ile Tyr Leu Glu Arg Tyr Glu Arg Asp Val Arg Asn His Asp
            500                 505                 510
Gln Asp Pro Gln Val Ala Leu Ala Glu Leu Ile Glu Ile Ala Glu Gln
        515                 520                 525
Leu Cys Gln Val Lys Gln Arg Thr Gly Arg Thr Glu Pro Ser Val Ile
        530                 535                 540
Thr
545

<210> SEQ ID NO 13
<211> LENGTH: 1387
<212> TYPE: DNA
<213> ORGANISM: METHYLOMONAS SP.

<400> SEQUENCE: 13
ccgaaagcag gcaaaatcac ggttcatttt tttttgtcat ccgtcaaaga caatccttat      60
aatgaggtaa tcgttctcct cgctacatct ggcactaaag cttccgaaga ctctttatcc     120
ggttcacaca aaataatat gtccaaatta atcaactctg ccgaatggaa cgccgtcaaa     180
caacatcatc aagaaattgc tggtaaattt tgcatgaaag aggcttttgc caaagatccc     240
cagcgtttcg ataaattctc cgtcaccttt aacgacatat tattagacta ttccaaaaac     300
ctgatcgacg agcgcaccat gcccttgctg atcgcattgg caaagcgggc agacttgcgc     360
```

```
gagaaaacgg aagcgatgtt ttccggctcc atcatcaaca ccaccgaaaa acgcgcggtt        420
ttgcataccg cgctgcgaaa ccgtagcaat acgcccgttt tcttccgcgg ccaggatgtc        480
atgccggaaa tcaacaaggt tctggcaaaa atgcgggttt tcgtggaaca ggtgcgttcg        540
ggccaatgga cgggctatag cggcaaggcc attaccgata tcgtcaacat cggcattggc        600
ggctcggatc tcggcccgaa aatggtcgac accgccttga cgccgtacgg caaaaacggc        660
ttaaaagcgc atttcgtatc caatgtcgat caaaccgaca tcgtcgaaac cctgaaaccg        720
ctcaatccgg aaaccacgct gttcctgatt tcatcgaaaa cgtttaccac gcaggaaacc        780
atgaccaatg cgcgctcggc acgtaactgg ttcatgaatg ccgcgcaaga tcccgcccat        840
atcaagaaac atttcatcgc catttccacc aacgaagaaa tggtcaagga attcggcatc        900
gacccggcga acatgttcga gttctgggac tgggtcggcg gcgttattc gctctggtcg        960 gtcatcggca tgtcgatagc tttatatatc ggcatggaca atttcgaaga actgctgatg       1020
ggtgcgcact tggccgacga acatttccgc catgcgccct acgaggaaaa cattccggtc       1080
atcatgggct tgctcggcat ctggtacaac aacttcttcg aagcgaaaac ctatgccatt       1140
ttgccgtatg cgcaatcctt gaaatatttt gccgattatt tccagcaagg cgacatggaa       1200
agcaacggca aaagcgcgac gatcaccggt gaaaaagtcg attacaacac gggcccccatc      1260 atctggggac agcccggcac caatggtcag cacgccttct ttcaattgat tcaccaaggc       1320
accaaactgg ttcccggcga ttttctggcg gccgcgcaaa gtcagtatga tttaccggat       1380
caccacg                                                                 1387
```

<210> SEQ ID NO 14
<211> LENGTH: 592
<212> TYPE: PRT
<213> ORGANISM: METHYLOMONAS SP.

<400> SEQUENCE: 14

```
Pro Lys Ala Gly Lys Ile Thr Val His Phe Phe Leu Ser Ser Val Lys
  1               5                  10                  15

Asp Asn Pro Tyr Asn Glu Val Ile Val Leu Leu Ala Thr Ser Gly Thr
             20                  25                  30

Lys Ala Ser Glu Asp Ser Leu Ser Gly Ser His Lys Asn Asn Met Ser
         35                  40                  45

Lys Leu Ile Asn Ser Ala Glu Trp Asn Ala Val Lys Gln His His Gln
     50                  55                  60

Glu Ile Ala Gly Lys Phe Cys Met Lys Glu Ala Phe Ala Lys Asp Pro
 65                  70                  75                  80

Gln Arg Phe Asp Lys Phe Ser Val Thr Phe Asn Asp Ile Leu Leu Asp
                 85                  90                  95

Tyr Ser Lys Asn Leu Ile Asp Glu Arg Thr Met Pro Leu Leu Ile Ala
            100                 105                 110

Leu Ala Lys Arg Ala Asp Leu Arg Glu Lys Thr Glu Ala Met Phe Ser
        115                 120                 125

Gly Ser Ile Ile Asn Thr Thr Glu Lys Arg Ala Val Leu His Thr Ala
    130                 135                 140

Leu Arg Asn Arg Ser Asn Thr Pro Val Phe Phe Arg Gly Gln Asp Val
145                 150                 155                 160

Met Pro Glu Ile Asn Lys Val Leu Ala Lys Met Arg Val Phe Val Glu
                165                 170                 175

Gln Val Arg Ser Gly Gln Trp Thr Gly Tyr Ser Gly Lys Ala Ile Thr
```

```
                180             185              190
Asp Ile Val Asn Ile Gly Ile Gly Gly Ser Asp Leu Gly Pro Lys Met
                195                 200                 205
Val Asp Thr Ala Leu Thr Pro Tyr Gly Lys Asn Gly Leu Lys Ala His
                210                 215                 220
Phe Val Ser Asn Val Asp Gln Thr Asp Ile Val Glu Thr Leu Lys Pro
225                 230                 235                 240
Leu Asn Pro Glu Thr Thr Leu Phe Leu Ile Ser Ser Lys Thr Phe Thr
                    245                 250                 255
Thr Gln Glu Thr Met Thr Asn Ala Arg Ser Ala Arg Asn Trp Phe Met
                260                 265                 270
Asn Ala Ala Gln Asp Pro Ala His Ile Lys Lys His Phe Ile Ala Ile
                275                 280                 285
Ser Thr Asn Glu Glu Met Val Lys Glu Phe Gly Ile Asp Pro Ala Asn
                290                 295                 300
Met Phe Glu Phe Trp Asp Trp Val Gly Gly Arg Tyr Ser Leu Trp Ser
305                 310                 315                 320
Val Ile Gly Met Ser Ile Ala Leu Tyr Ile Gly Met Asp Asn Phe Glu
                    325                 330                 335
Glu Leu Leu Met Gly Ala His Leu Ala Asp Glu His Phe Arg His Ala
                340                 345                 350
Pro Tyr Glu Glu Asn Ile Pro Val Ile Met Gly Leu Leu Gly Ile Trp
                355                 360                 365
Tyr Asn Asn Phe Phe Glu Ala Glu Thr Tyr Ala Ile Leu Pro Tyr Ala
370                 375                 380
Gln Ser Leu Lys Tyr Phe Ala Asp Tyr Phe Gln Gln Gly Asp Met Glu
385                 390                 395                 400
Ser Asn Gly Lys Ser Ala Thr Ile Thr Gly Glu Lys Val Asp Tyr Asn
                    405                 410                 415
Thr Gly Pro Ile Ile Trp Gly Gln Pro Gly Thr Asn Gly Gln His Ala
                420                 425                 430
Phe Phe Gln Leu Ile His Gln Gly Thr Lys Leu Val Pro Gly Asp Phe
                435                 440                 445
Leu Ala Ala Ala Gln Ser Gln Tyr Asp Leu Pro Asp His His Asp Ile
450                 455                 460
Leu Ile Ser Asn Phe Leu Ala Gln Ala Glu Ala Leu Met Arg Gly Lys
465                 470                 475                 480
Thr Glu Glu Glu Val Arg Gln Asp Leu Ser His Glu Pro Asn Leu Asp
                    485                 490                 495
Asp Ala Leu Ile Ala Ser Lys Ile Phe Glu Gly Asn Lys Pro Ser Asn
                500                 505                 510
Ser Phe Leu Phe Lys Lys Leu Thr Pro Arg Thr Leu Gly Thr Leu Ile
                515                 520                 525
Ala Phe Tyr Glu His Lys Ile Phe Val Gln Gly Val Ile Trp Asn Ile
                530                 535                 540
Asn Ser Phe Asp Gln Met Gly Val Glu Leu Gly Lys Val Leu Ala Lys
545                 550                 555                 560
Ala Ile Leu Pro Glu Leu Lys Asn Asp Ile Ile Ala Ser His Asp
                    565                 570                 575
Ser Ser Thr Asn Gly Leu Ile Asn Thr Tyr Lys Arg Leu Arg Lys Ala
                580                 585                 590

<210> SEQ ID NO 15
```

<211> LENGTH: 1311
<212> TYPE: DNA
<213> ORGANISM: METHYLOMONAS SP.

<400> SEQUENCE: 15

```
gatgtggtca catggcccta tcacttaacg gctgatattc gattttgtca ttggttttt     60
cttaactta acttctacac gctcatgaac aaacctaaaa agttgcaat actgacagca      120
ggcggcttgg cgccttgttt gaattccgca atcggtagtt tgatcgaacg ttataccgaa    180
atcgatccta gcatagaaat catttgctat cgcggcggtt ataaaggcct gttgctgggc    240
gattcttatc cagtaacggc cgaagtgcgt aaaaaggcgg tgttctgca acgttttggc     300
ggttctgtga tcggcaacag ccgcgtcaaa ttgaccaatg tcaaagactg cgtgaaacgc    360
ggtttggtca agagggtga agatccgcaa aaagtcgcgg ctgatcaatt ggttaaggat    420
ggtgtcgata ttctgcacac catcggcggc gatgatacca atacggcagc agcggatttg    480
gcagcattcc tggccagaaa taattacgga ctgaccgtca ttggtttacc taaaaccgtc    540
gataacgacg tatttccgat caagcaatca ctaggtgctt ggactgccgc cgagcaaggc    600
gcgcgttatt tcatgaacgt ggtggccgaa acaacgcca acccacgcat gctgatcgta    660
cacgaagtga tgggccgtaa ctgcggctgg ctgaccgctg caaccgcgca ggaatatcgc    720
aaattactgg accgtgccga gtggttgccg gaattgggtt tgactcgtga atcttatgaa    780
gtgcacgcgg tattcgttcc ggaaatggcg atcgacctgg aagccgaagc caagcgcctg    840
cgcgaagtga tggacaaagt cgattgcgtc aacatcttcg tttccgaagg tgccggcgtc    900
gaagctatcg tcgcggaaat gcaggccaaa ggccaggaag tgccgcgcga tgcgttcggc    960
cacatcaaac tggatgcggt caaccctggt aaatggttcg gcgagcaatt cgcgcagatg   1020
ataggcgcgg aaaaaaccct ggtacaaaaa tcgggatact tcgcccgtgc ttctgcttcc   1080
aacgttgacg acatgcgttt gatcaaatcg tgcgccgact ggcggtcga gtgcgcgttc    1140
cgccgcgagt ctggcgtgat cggtcacgac gaagacaacg gcaacgtgtt gcgtgcgatc   1200
gagtttccgc gcatcaaggg cggcaaaccg ttcaatatcg acaccgactg gttcaatagc   1260
atgttgagcg aaatcggcca gcctaaaggc ggtaaagtcg aagtcagcca c             1311
```

<210> SEQ ID NO 16
<211> LENGTH: 437
<212> TYPE: PRT
<213> ORGANISM: METHYLOMONAS SP.

<400> SEQUENCE: 16

```
Asp Val Val Thr Trp Pro Tyr His Leu Thr Ala Asp Ile Arg Phe Cys
 1               5                  10                  15

His Trp Phe Phe Leu Asn Phe Asn Phe Tyr Thr Leu Met Asn Lys Pro
            20                  25                  30

Lys Lys Val Ala Ile Leu Thr Ala Gly Gly Leu Ala Pro Cys Leu Asn
        35                  40                  45

Ser Ala Ile Gly Ser Leu Ile Glu Arg Tyr Thr Glu Ile Asp Pro Ser
    50                  55                  60

Ile Glu Ile Ile Cys Tyr Arg Gly Gly Tyr Lys Gly Leu Leu Leu Gly
65                  70                  75                  80

Asp Ser Tyr Pro Val Thr Ala Glu Val Arg Lys Lys Ala Gly Val Leu
                85                  90                  95

Gln Arg Phe Gly Gly Ser Val Ile Gly Asn Ser Arg Val Lys Leu Thr
            100                 105                 110
```

```
Asn Val Lys Asp Cys Val Lys Arg Gly Leu Val Lys Glu Gly Glu Asp
            115                 120                 125

Pro Gln Lys Val Ala Ala Asp Gln Leu Val Lys Asp Gly Val Asp Ile
            130                 135                 140

Leu His Thr Ile Gly Gly Asp Thr Asn Thr Ala Ala Ala Asp Leu
145                 150                 155                 160

Ala Ala Phe Leu Ala Arg Asn Asn Tyr Gly Leu Thr Val Ile Gly Leu
                165                 170                 175

Pro Lys Thr Val Asp Asn Asp Val Phe Pro Ile Lys Gln Ser Leu Gly
            180                 185                 190

Ala Trp Thr Ala Ala Glu Gln Gly Ala Arg Tyr Phe Met Asn Val Val
            195                 200                 205

Ala Glu Asn Asn Ala Asn Pro Arg Met Leu Ile Val His Glu Val Met
210                 215                 220

Gly Arg Asn Cys Gly Trp Leu Thr Ala Ala Thr Ala Gln Glu Tyr Arg
225                 230                 235                 240

Lys Leu Leu Asp Arg Ala Glu Trp Leu Pro Glu Leu Gly Leu Thr Arg
                245                 250                 255

Glu Ser Tyr Glu Val His Ala Val Phe Val Pro Glu Met ala Ile Asp
            260                 265                 270

Leu Glu Ala Glu Ala Lys Arg Leu Arg Glu Val Met Asp Lys Val Asp
            275                 280                 285

Cys Val Asn Ile Phe Val Ser Glu Gly Ala Gly Val Glu Ala Ile Val
            290                 295                 300

Ala Glu Met Gln Ala Lys Gly Gln Glu Val Pro Arg Asp Ala Phe Gly
305                 310                 315                 320

His Ile Lys Leu Asp Ala Val Asn Pro Gly Lys Trp Phe Gly Glu Gln
                325                 330                 335

Phe Ala Gln Met Ile Gly Ala Glu Lys Thr Leu Val Gln Lys Ser Gly
            340                 345                 350

Tyr Phe Ala Arg Ala Ser Ala Ser Asn Val Asp Asp Met Arg Leu Ile
            355                 360                 365

Lys Ser Cys Ala Asp Leu Ala Val Glu Cys Ala Phe Arg Arg Glu Ser
            370                 375                 380

Gly Val Ile Gly His Asp Glu Asp Asn Gly Asn Val Leu Arg Ala Ile
385                 390                 395                 400

Glu Phe Pro Arg Ile Lys Gly Gly Lys Pro Phe Asn Ile Asp Thr Asp
                405                 410                 415

Trp Phe Asn Ser Met Leu Ser Glu Ile Gly Gln Pro Lys Gly Gly Lys
            420                 425                 430

Val Glu Val Ser His
            435

<210> SEQ ID NO 17
<211> LENGTH: 1360
<212> TYPE: DNA
<213> ORGANISM: METHYLOMONAS SP.

<400> SEQUENCE: 17
agtgtcccgc actcgcatca cccggagaca tccttaatgc atcccgtact cgaaaaagtc      60
acagaacaag tcatcgcccg cagccgggaa acccgtgccg cttatctgaa gcgcatagag     120
gccgccatcg ccgaaggccc gcaacgcaat aaactgcctt gcgccaatct ggcccacggt     180
ttcgcggtct gttcggccat cgaaaaagaa gaattgtctc atggcccaa gcccaatgtc     240
```

-continued

```
ggcatcatct cggcctacaa cgacatgctg tccgcgcacg aaccctacaa ggattatcct    300
gccctgatca aacaggccgt gcgcgaagcc ggcggcgtgg ctcaattcgc cggcggcgtg    360
cccgcgatgt gcgacggcgt cacccagggc atgccgggca tggaattgtc gctattcagc    420
cgcgacgtca tcgcgatgtc caccgcgatc ggcctggctc ataacatgtt cgacgcggcg    480
ctgtatctgg gcgtctgcga caagatcgta cccggtttgt tgatcggtgc attgagcttc    540
ggccatttgc cggccgtttt cttgccagcc ggccccatga ccagcggcct gtccaacaag    600
gaaaaatccc gtgcccggca aaatacgcc gaaggtaaga tcggtgaaaa agaattgctg    660
gaatcggaag ccaagtctta ccacagccca ggcacctgca ccttctatgg caccgccaac    720
agcaaccaga tgatggtcga gatcatgggc ctgcacctgc ccggtagttc cttcatcaat    780
ccttacaccc cactgcgcga cgaactgacc aaggccgccg ccaggcaggt gttgaaattc    840
accgcgctgg gcaacgactt caggccaatc gcgcatgtga tcgacgaaaa agccatcatc    900
aatgccatca tcggcttgct ggcgaccggc ggttcgacca accataccat ccatttgatc    960
gcgattgccc gcgccgccgg catcatcatc aactgggacg atttcgacgc cctatccaaa   1020
gtcattccgt tgctgaccaa gatctatccg aacggcccgg ccgacgtcaa ccaattccag   1080
gcggccggcg gcatgagctt attgatacac gaactgctgg atcacggctt gttgcacggc   1140
gacatcctga ccataggcga ccagcgcggc atggcccaat acagtcaagt accgacgctg   1200
caagacggcc aattacaatg gcagcccggt cctaccgcat cgcgcgatcc cgaaatcatc   1260
gccagcgtgg caaaaccttt cgccgccggt ggtggcctgc atgtgatgca tggcaatctg   1320
ggccgcggcg tatccaagat ttccgccgtc tccgaagatc                         1360
```

<210> SEQ ID NO 18
<211> LENGTH: 618
<212> TYPE: PRT
<213> ORGANISM: METHYLOMONAS SP.

<400> SEQUENCE: 18

```
Ser Val Pro His Ser His Pro Glu Thr Ser Leu Met His Pro Val
 1               5                  10                  15

Leu Glu Lys Val Thr Glu Gln Val Ile Ala Arg Ser Arg Glu Thr Arg
            20                  25                  30

Ala Ala Tyr Leu Lys Arg Ile Glu Ala Ala Ile Ala Glu Gly Pro Gln
        35                  40                  45

Arg Asn Lys Leu Pro Cys Ala Asn Leu Ala His Gly Phe Ala Val Cys
    50                  55                  60

Ser Ala Ile Glu Lys Glu Glu Leu Ser His Gly Pro Lys Pro Asn Val
65                  70                  75                  80

Gly Ile Ile Ser Ala Tyr Asn Asp Met Leu Ser Ala His Glu Pro Tyr
                85                  90                  95

Lys Asp Tyr Pro Ala Leu Ile Lys Gln Ala Val Arg Glu Ala Gly Gly
            100                 105                 110

Val Ala Gln Phe Ala Gly Gly Val Pro Ala Met Cys Asp Gly Val Thr
        115                 120                 125

Gln Gly Met Pro Gly Met Glu Leu Ser Leu Phe Ser Arg Asp Val Ile
    130                 135                 140

Ala Met Ser Thr Ala Ile Gly Leu Ala His Asn Met Phe Asp Ala Ala
145                 150                 155                 160

Leu Tyr Leu Gly Val Cys Asp Lys Ile Val Pro Gly Leu Leu Ile Gly
                165                 170                 175
```

```
Ala Leu Ser Phe Gly His Leu Pro Ala Val Phe Leu Pro Ala Gly Pro
            180                 185                 190

Met Thr Ser Gly Leu Ser Asn Lys Glu Lys Ser Arg Ala Arg Gln Lys
            195                 200                 205

Tyr Ala Glu Gly Lys Ile Gly Glu Lys Glu Leu Leu Glu Ser Glu Ala
        210                 215                 220

Lys Ser Tyr His Ser Pro Gly Thr Cys Thr Phe Tyr Gly Thr Ala Asn
225                 230                 235                 240

Ser Asn Gln Met Met Val Glu Ile Met Gly Leu His Leu Pro Gly Ser
                245                 250                 255

Ser Phe Ile Asn Pro Tyr Thr Pro Leu Arg Asp Glu Leu Thr Lys Ala
                260                 265                 270

Ala Ala Arg Gln Val Leu Lys Phe Thr Ala Leu Gly Asn Asp Phe Arg
            275                 280                 285

Pro Ile Ala His Val Ile Asp Glu Lys Ala Ile Ile Asn Ala Ile Ile
        290                 295                 300

Gly Leu Leu Ala Thr Gly Gly Ser Thr Asn His Thr Ile His Leu Ile
305                 310                 315                 320

Ala Ile Ala Arg Ala Ala Gly Ile Ile Ile Asn Trp Asp Asp Phe Asp
                325                 330                 335

Ala Leu Ser Lys Val Ile Pro Leu Leu Thr Lys Ile Tyr Pro Asn Gly
            340                 345                 350

Pro Ala Asp Val Asn Gln Phe Gln Ala Ala Gly Gly Met Ser Leu Leu
        355                 360                 365

Ile His Glu Leu Leu Asp His Gly Leu Leu His Gly Asp Ile Leu Thr
    370                 375                 380

Ile Gly Asp Gln Arg Gly Met ala Gln Tyr Ser Gln Val Pro Thr Leu
385                 390                 395                 400

Gln Asp Gly Gln Leu Gln Trp Gln Pro Gly Pro Thr Ala Ser Arg Asp
                405                 410                 415

Pro Glu Ile Ile Ala Ser Val Ala Lys Pro Phe Ala Ala Gly Gly Gly
            420                 425                 430

Leu His Val Met His Gly Asn Leu Gly Arg Gly Val Ser Lys Ile Ser
        435                 440                 445

Ala Val Ser Glu Asp His Gln Val Val Thr Ala Pro Ala Met Val Phe
    450                 455                 460

Asp Asp Gln Leu Asp Val Val Ala Ala Phe Lys Arg Gly Glu Leu Glu
465                 470                 475                 480

Lys Asp Val Ile Val Val Leu Arg Phe Gln Gly Pro Lys Ala Asn Gly
                485                 490                 495

Met Pro Glu Leu His Lys Leu Thr Pro Val Leu Gly Val Leu Gln Asp
            500                 505                 510

Arg Gly Phe Lys Val Gly Leu Leu Thr Asp Gly Arg Met Ser Gly Ala
        515                 520                 525

Ser Gly Lys Val Pro Ser Ala Ile His Met Trp Pro Glu Cys Ile Asp
    530                 535                 540

Gly Gly Pro Leu Ala Lys Val Arg Asp Gly Asp Ile Ile Val Met Asn
545                 550                 555                 560

Thr Gln Thr Gly Glu Val Asn Val Gln Val Asp Pro Ala Glu Phe Lys
                565                 570                 575

Ala Arg Val Ala Glu Pro Asn His Ala Thr Gly His His Phe Gly Met
            580                 585                 590

Gly Arg Glu Leu Phe Gly Ala Met Arg Ala Gln Ala Ser Thr Ala Glu
```

-continued

```
        595             600             605
Thr Gly Ala Thr Asn Leu Phe Phe Val Asp
        610             615

<210> SEQ ID NO 19
<211> LENGTH: 1477
<212> TYPE: DNA
<213> ORGANISM: METHYLOMONAS SP.

<400> SEQUENCE: 19
atggcattgg gcttttttgct ccgtagcccc aaagacatga caaaaaacat tacttacaaa      60
ccctgcgacc tggtgattta cggcgcactg gcgatttat ccaaacgtaa actactgatt       120
tcattatacc gtttggaaaa acacaatctg ctcgagcccg atacgcgcat catcggcgta      180
gatcgtttgg aagaaaccag cgacagtttc gtcgaaattg cgcacaaaag cttgcaggcg      240
tttttgaaca acgtcatcga cgcagaaatc tggcaacgtt tttccaaacg cttgtcctat      300
ttgaaaatcg atctgaccca acccgagcaa tacaaacaac tgcatacggt cgtcgatgcc      360
gaaaaacgag tcatggtgaa ttatttcgcg gtggcaccct ttttgttcaa aaacatttgc      420
caaggcttgc atgactgcgg cgtattgacg gccgaatcgc gcatggtgat ggaaaaaccc      480
atcggccacg acctgaaatc gtcgaaagaa atcaacgacg tcgtcgccga cgtattccac      540
gaagaccagg tctaccgcat cgaccactac ctgggcaagg aaacggtctt gaacttgctg      600
gccttgcgtt tcgccaattc gatattcacg accaactgga atcacaacac gatagaccat      660
atccagatta cggtcggtga ggacatcggc atcgagggcc gttgggaata tttcgacaag      720
accggccaat tgcgcgacat gctgcaaaac catttgctgc aaatcctgac cttcgtcgcg      780
atggagccgc ccgcggatct gtcggccgaa agcatacaca tggaaaaaat caaggtcctg      840
aaagccttgc ggccaatcac cgtgcgcaat gtcgaggaaa aaaccgtgcg cggtcaatac      900
accgccggtt tcatcaaagg caagtcggta ccgggttatc tggaagaaga aggtgccaac      960
accgaaagca cgaccgaaac tttcgtcgcg atccgcgtgg atatcgataa ctggcgctgg     1020
gccggtgtcc cgttttacat gcgtaccggc aaacgcacgc ccaacaaacg caccgagatt     1080
gtggtcaatt tcaagcaatt gccgcacaac atcttcaagg acagttttca tgaactgccg     1140
gccaataaac tggtcattca tttgcaaccg aacgaagggg tggatgtcat gatgttgaac     1200
aaggtgccgg gcatagacgg caacatcaag ttgcaacaga ccaaactgga tttgagcttt     1260
tccgaaacct tcaagaaaaa ccgaattttc ggcggctacg aaaaactgat tctggaagcc     1320
ctgcgcggca acccgacgct gttttttgagc cgcgaggaaa tagaacaagc ctggacctgg     1380
gtcgattcga ttcaggatgc ctggcaacac aaccacacgc cacccaaacc ctatcccgcg     1440
ggtagctggg gtccagtggc atcggtcgca ttactgg                              1477

<210> SEQ ID NO 20
<211> LENGTH: 501
<212> TYPE: PRT
<213> ORGANISM: METHYLOMONAS SP.

<400> SEQUENCE: 20

Met ala Leu Gly Phe Leu Leu Arg Ser Pro Lys Asp Met Thr Lys Asn
  1               5                  10                  15

Ile Thr Tyr Lys Pro Cys Asp Leu Val Ile Tyr Gly Ala Leu Gly Asp
                 20                  25                  30

Leu Ser Lys Arg Lys Leu Leu Ile Ser Leu Tyr Arg Leu Glu Lys His
         35                  40                  45
```

```
Asn Leu Leu Glu Pro Asp Thr Arg Ile Ile Gly Val Asp Arg Leu Glu
 50                  55                  60
Glu Thr Ser Asp Ser Phe Val Glu Ile Ala His Lys Ser Leu Gln Ala
 65                  70                  75                  80
Phe Leu Asn Asn Val Ile Asp Ala Glu Ile Trp Gln Arg Phe Ser Lys
                 85                  90                  95
Arg Leu Ser Tyr Leu Lys Ile Asp Leu Thr Gln Pro Glu Gln Tyr Lys
            100                 105                 110
Gln Leu His Thr Val Val Asp Ala Glu Lys Arg Val Met Val Asn Tyr
        115                 120                 125
Phe Ala Val Ala Pro Phe Leu Phe Lys Asn Ile Cys Gln Gly Leu His
130                 135                 140
Asp Cys Gly Val Leu Thr Ala Glu Ser Arg Met Val Met Glu Lys Pro
145                 150                 155                 160
Ile Gly His Asp Leu Lys Ser Ser Lys Glu Ile Asn Asp Val Val Ala
                165                 170                 175
Asp Val Phe His Glu Asp Gln Val Tyr Arg Ile Asp His Tyr Leu Gly
            180                 185                 190
Lys Glu Thr Val Leu Asn Leu Ala Leu Arg Phe Ala Asn Ser Ile
        195                 200                 205
Phe Thr Thr Asn Trp Asn His Asn Thr Ile Asp His Ile Gln Ile Thr
210                 215                 220
Val Gly Glu Asp Ile Gly Ile Glu Gly Arg Trp Glu Tyr Phe Asp Lys
225                 230                 235                 240
Thr Gly Gln Leu Arg Asp Met Leu Gln Asn His Leu Leu Gln Ile Leu
                245                 250                 255
Thr Phe Val Ala Met Glu Pro Pro Ala Asp Leu Ser Ala Glu Ser Ile
            260                 265                 270
His Met Glu Lys Ile Lys Val Leu Lys Ala Leu Arg Pro Ile Thr Val
        275                 280                 285
Arg Asn Val Glu Glu Lys Thr Val Arg Gly Gln Tyr Thr Ala Gly Phe
290                 295                 300
Ile Lys Gly Lys Ser Val Pro Gly Tyr Leu Glu Glu Gly Ala Asn
305                 310                 315                 320
Thr Glu Ser Thr Thr Glu Thr Phe Val Ala Ile Arg Val Asp Ile Asp
                325                 330                 335
Asn Trp Arg Trp Ala Gly Val Pro Phe Tyr Met Arg Thr Gly Lys Arg
            340                 345                 350
Thr Pro Asn Lys Arg Thr Glu Ile Val Val Asn Phe Lys Gln Leu Pro
        355                 360                 365
His Asn Ile Phe Lys Asp Ser Phe His Glu Leu Pro Ala Asn Lys Leu
370                 375                 380
Val Ile His Leu Gln Pro Asn Glu Gly Val Asp Val Met Met Leu Asn
385                 390                 395                 400
Lys Val Pro Gly Ile Asp Gly Asn Ile Lys Leu Gln Gln Thr Lys Leu
                405                 410                 415
Asp Leu Ser Phe Ser Glu Thr Phe Lys Lys Asn Arg Ile Phe Gly Gly
            420                 425                 430
Tyr Glu Lys Leu Ile Leu Glu Ala Leu Arg Gly Asn Pro Thr Leu Phe
        435                 440                 445
Leu Ser Arg Glu Glu Ile Glu Gln Ala Trp Thr Trp Val Asp Ser Ile
450                 455                 460
```

-continued

```
Gln Asp Ala Trp Gln His Asn His Thr Pro Pro Lys Pro Tyr Pro Ala
465                 470                 475                 480

Gly Ser Trp Gly Pro Val Ala Ser Val Ala Leu Leu Ala Arg Asp Gly
                485                 490                 495

Arg Ala Trp Glu Glu
                500
```